(12) United States Patent
Shah et al.

(10) Patent No.: US 8,580,119 B1
(45) Date of Patent: *Nov. 12, 2013

(54) TRANSESTERIFICATION OF BIODIESEL FEEDSTOCK WITH SOLID HETEROGENEOUS CATALYST

(71) Applicant: Menlo Energy Management, LLC, San Francisco, CA (US)

(72) Inventors: Gaurav Shah, Fremont, CA (US); Sunil Suri, Woodside, CA (US)

(73) Assignee: Menlo Energy Management, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,772

(22) Filed: Nov. 27, 2012

(51) Int. Cl.
*C10L 1/19* (2006.01)
*C07C 27/26* (2006.01)
*C12P 7/00* (2006.01)

(52) U.S. Cl.
USPC ............ 210/669; 44/308; 44/605; 210/770; 210/806; 554/175; 568/861; 568/885; 585/800

(58) Field of Classification Search
USPC ........... 44/307, 308, 605, 606; 210/641, 650, 210/651, 739, 767, 770, 805, 806, 663, 210/669; 203/39, 41, 44, 47, 71, 73, 74, 81; 585/240, 14, 800, 833; 560/1, 96, 98, 560/191; 554/174, 175; 568/858–861, 872, 568/884, 885; 435/134, 135, 157, 161–163
See application file for complete search history.

(56) References Cited

U.S. PATENT DOCUMENTS

| | | | |
|---|---|---|---|
| 4,698,186 A | 10/1987 | Jeromin et al. | |
| 5,525,126 A * | 6/1996 | Basu et al. | 44/308 |
| 5,945,318 A * | 8/1999 | Breivik et al. | 435/134 |
| 6,878,837 B2 | 4/2005 | Bournay et al. | |
| 7,112,229 B2 * | 9/2006 | Khalil et al. | 44/308 |
| 7,579,493 B2 | 8/2009 | Gutsche et al. | |
| 7,695,533 B2 * | 4/2010 | Kovacs et al. | 44/308 |
| 7,700,793 B2 | 4/2010 | Iyer | |
| 7,754,931 B2 * | 7/2010 | Monnier et al. | 585/240 |
| 7,795,460 B2 * | 9/2010 | Elliott | 554/167 |
| 7,851,645 B2 * | 12/2010 | Ryu | 558/274 |
| 7,943,791 B2 * | 5/2011 | Mcneff | 554/174 |
| 8,088,183 B2 * | 1/2012 | Jackam et al. | 44/308 |
| 8,137,555 B2 * | 3/2012 | Kale | 210/601 |
| 2005/0204612 A1 * | 9/2005 | Connemann et al. | 44/437 |
| 2007/0158270 A1 * | 7/2007 | Geier et al. | 210/656 |
| 2007/0232818 A1 * | 10/2007 | Crawford et al. | 554/174 |
| 2008/0289248 A1 * | 11/2008 | Gao | 44/308 |
| 2008/0312468 A1 | 12/2008 | Fleisher | |

(Continued)

FOREIGN PATENT DOCUMENTS

DE 19600025 A1 7/1997
JP 2002-088392 * 3/2002

OTHER PUBLICATIONS

Translated Abstract for Publication No. RD 509012, Published Sep. 10, 2006, Anonymous Inventor.*
Derwent Abstract for JP 2002-088392, printed May 28, 2013.*

*Primary Examiner* — Joseph Drodge
(74) *Attorney, Agent, or Firm* — Schwegman Lundberg & Woessner PA

(57) ABSTRACT

Process and steps for the production of biodiesel and/or glycerin from feedstock are provided.

30 Claims, 6 Drawing Sheets

(56) References Cited

U.S. PATENT DOCUMENTS

| | | | |
|---|---|---|---|
| 2009/0056201 A1* | 3/2009 | Morgan | 44/308 |
| 2009/0064567 A1* | 3/2009 | Lippmeier et al. | 44/308 |
| 2009/0234146 A1* | 9/2009 | Cooney et al. | 554/174 |
| 2009/0294358 A1 | 12/2009 | Dietrich et al. | |
| 2010/0151535 A1* | 6/2010 | Franklin et al. | 435/128 |
| 2010/0312023 A1* | 12/2010 | Henkelmann et al. | 568/858 |
| 2011/0113677 A1* | 5/2011 | Woods | 44/307 |
| 2011/0154720 A1* | 6/2011 | Bartek et al. | 44/307 |
| 2011/0162951 A1* | 7/2011 | Berry et al. | 201/36 |
| 2011/0165634 A1* | 7/2011 | Franklin et al. | 435/123 |
| 2011/0185624 A1* | 8/2011 | Hall | 44/307 |
| 2011/0192073 A1* | 8/2011 | Kale | 44/307 |
| 2011/0220483 A1* | 9/2011 | Margnat et al. | 203/34 |
| 2011/0245551 A1 | 10/2011 | Marker | |
| 2012/0029218 A1* | 2/2012 | Kim et al. | 554/174 |
| 2012/0079760 A1* | 4/2012 | Savage et al. | 44/388 |
| 2012/0151828 A1* | 6/2012 | Kalnes | 44/308 |
| 2012/0167454 A1* | 7/2012 | Brandvold et al. | 44/308 |
| 2012/0277496 A1* | 11/2012 | Lee et al. | 568/885 |
| 2012/0279111 A1* | 11/2012 | Blasco Garcia | 44/388 |
| 2012/0324784 A1* | 12/2012 | Franklin et al. | 44/308 |
| 2013/0052701 A1* | 2/2013 | Basheer et al. | 435/134 |

* cited by examiner

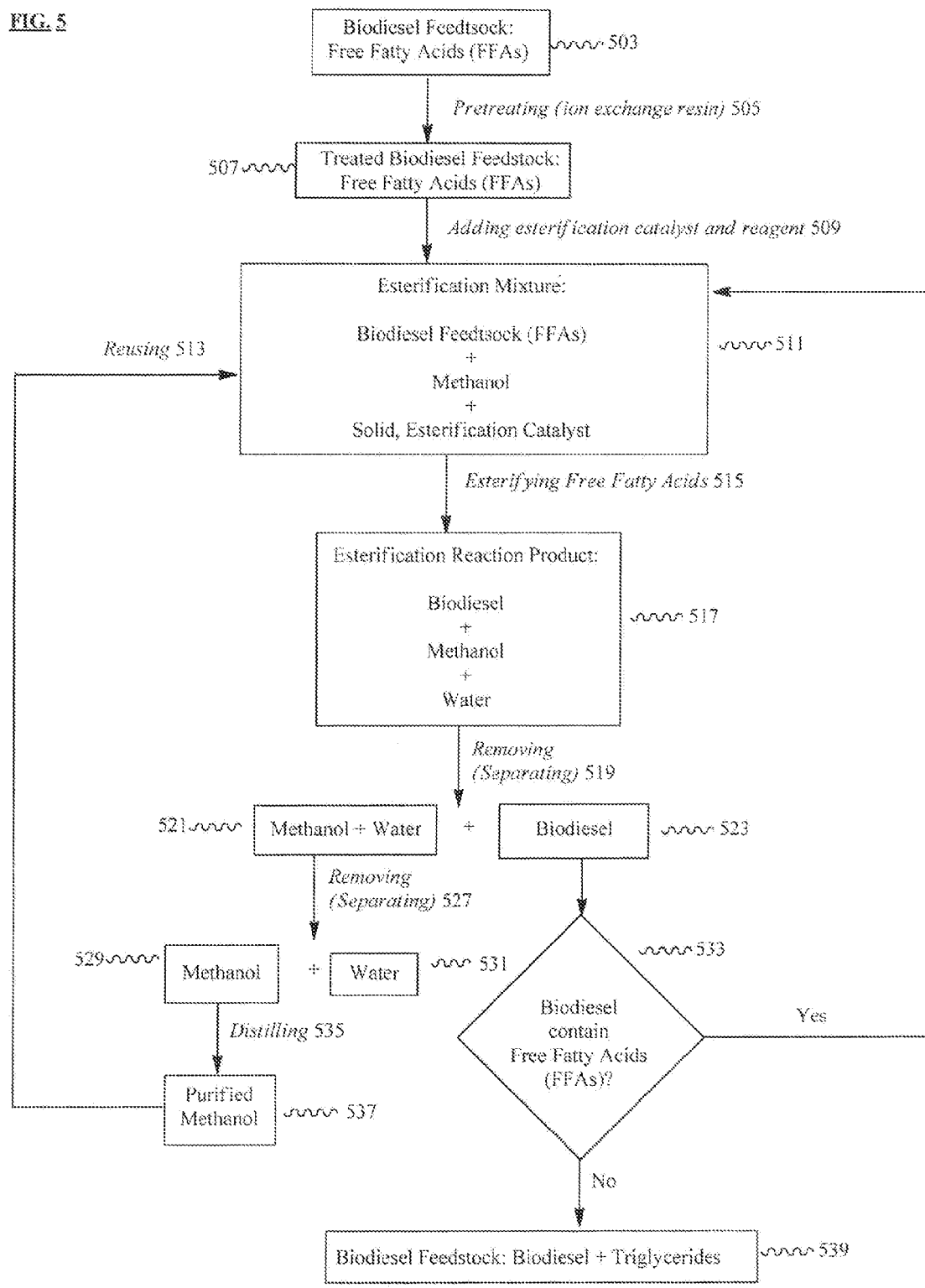

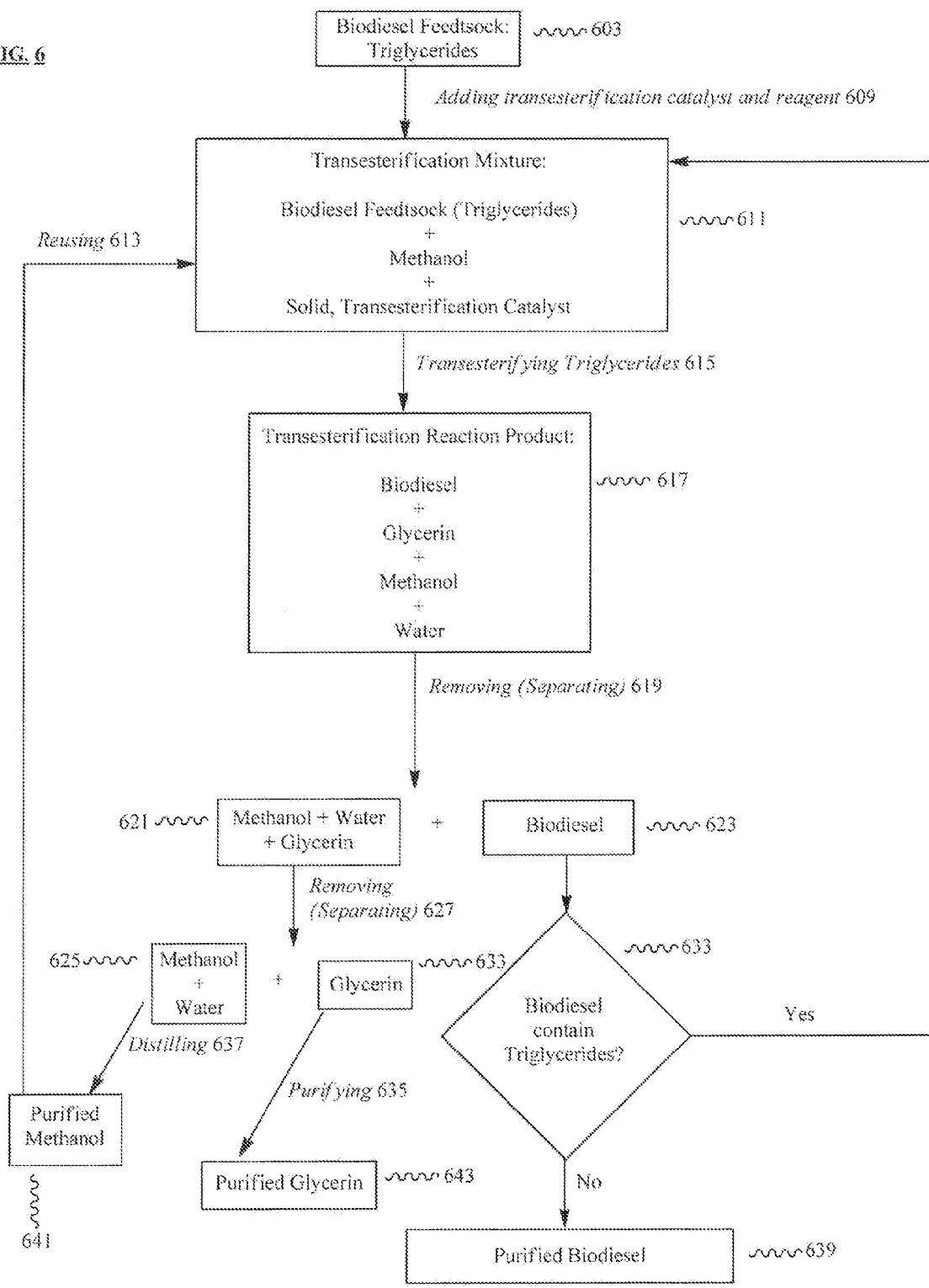

TRANSESTERIFICATION OF BIODIESEL FEEDSTOCK WITH SOLID HETEROGENEOUS CATALYST

BRIEF SUMMARY OF THE INVENTION

The present invention provides for a method to produce biodiesel and/or glycerin from biodiesel feedstock. The production of biodiesel and/or glycerin includes a pretreatment process, an esterification process and/or a transesterification process. The pretreatment process is employed to separate from the biodiesel feedstock, solid particles having a diameter of greater than about 2 microns. The pretreatment process can also be employed to separate from the biodiesel feedstock, impurities such as sulfur, phosphorous, phosphatides, gums, strerols, metals and/or other color bodies. When a biodiesel feedstock contains these impurities and/or solid particles having a diameter of greater than about 2 microns, the pretreatment process can be employed to separate them. A benefit of the pretreatment process is the ability to handle biodiesel feedstock having high levels of gums, phosphorous, sterols, sulfur, and/or color contaminants. The pretreatment process can significantly reduce the phosphorous and sulfur levels to below about 10 ppm in the treated feedstock. The pretreatment process can also significantly reduce the levels of chlorophyll, color bodies, gums, phosphatides, gums, sterols, and/or metals (e.g., calcium, magnesium, iron, copper, sodium, and potassium) in the treated feedstock.

The esterification process is employed when the biodiesel feedstock contains free fatty acids (FFAs). When the biodiesel feedstock contains FFAs, the esterification process can be employed to convert FFAs to biodiesel. With reference to biodiesel, free fatty acids present in the feedstock react with methanol in the presence of catalyst (and/or high heat and/or high pressure) to form biodiesel and water.

The transesterification process is employed when the biodiesel feedstock contains triglycerides. When the biodiesel feedstock contains triglycerides, the transesterification process can be employed to convert triglycerides to biodiesel and glycerin. With reference to biodiesel, triglycerides present in the feedstock react with methanol in the presence of catalyst (and/or high heat and/or high pressure) to form biodiesel and glycerin.

Pretreatment

The present invention provides for a pretreatment of biodiesel feedstock. The process includes:

(a) filtering a biodiesel feedstock, thereby separating from the feedstock solid particles having a diameter up to 2 microns, to provide a filtrate and a retentate;

(b) separating at least one of moisture and water from the filtrate, to provide a dried filtrate;

(c) distilling the dried filtrate, to provide a distillate and a residue;

(d) distilling the distillate to provide a subsequent distillate and optionally a subsequent residue; and;

(e) optionally repeating steps (c) and (d), one or more times, by distilling the subsequent distillate, to obtain a final distillate.

Esterification

The present invention also provides for an esterification of biodiesel feedstock. The process includes:

(a) contacting (i) methanol, (ii) a solid heterogeneous esterification catalyst, and (iii) a biodiesel feedstock including free fatty acids, wherein the contacting is carried out under conditions suitable to provide an esterification reaction product including biodiesel, methanol, water, and optionally free fatty acids;

(b) separating water and methanol from the esterification reaction product;

(c) contacting the esterification reaction product with (i) methanol and (iii) a solid heterogeneous esterification catalyst, wherein the contacting is carried out under conditions suitable to provide a subsequent esterification reaction product including biodiesel, methanol, water and optionally free fatty acids; and (d) optionally repeating steps (b) and (c) one or more times, to provide an esterification reaction product including biodiesel;

wherein the methanol separated from the one or more esterification reaction products is purified to a purity of at least about 99.9 wt. %, and is employed in a subsequent esterification.

Transesterification

The present invention also provides for a transesterification of biodiesel feedstock. The process includes:

(a) contacting at a temperature of less than 102° F. (38.89° C.) (i) methanol, (ii) a solid heterogeneous transesterification catalyst, and (iii) a biodiesel feedstock including triglycerides, wherein the contacting is carried out under conditions suitable to provide a biodiesel, methanol, water, glycerin and optionally triglycerides;

(b) separating water, glycerin and methanol from the transesterification reaction product;

(c) contacting the transesterification reaction product with (i) methanol and (ii) a solid heterogeneous transesterification catalyst, wherein the contacting is carried out under conditions suitable to provide a subsequent transesterification reaction product including biodiesel, methanol, water, glycerin and optionally triglycerides; and (d) optionally repeating steps (b) and (c) one or more times, to provide a transesterification reaction product including biodiesel and glycerin;

wherein the methanol separated from the one or more transesterification reaction products is purified to a purity of at least about 99.9 wt. %, and is employed in a subsequent transesterification.

Production of Biodiesel from Feedstock

The present invention also provides for the production of biodiesel from feedstock. The process includes:

(a) filtering a biodiesel feedstock, thereby separating from the feedstock solid particles having a diameter up to 2 microns, to provide a filtrate and a retentate;

(b) separating at least one of moisture and water from the filtrate, to provide a dried filtrate;

(c) distilling the dried filtrate, to provide a distillate and a residue;

(d) distilling the distillate to provide a subsequent distillate and optionally a subsequent residue;

(e) optionally repeating steps (c) and (d), one or more times, by distilling the subsequent distillate, to obtain a final distillate;

(f) passing final distillate through an ion exchange resin;

(g) contacting (i) methanol, (ii) a solid heterogeneous esterification catalyst, and (iii) the final distillate, wherein the contacting is carried out under conditions suitable to provide an esterification reaction product including biodiesel, methanol, water, and optionally free fatty acids;

(h) separating water and methanol from the esterification reaction product;

(i) contacting the esterification reaction product with (i) methanol and (ii) a solid heterogeneous esterification catalyst, wherein the contacting is carried out under conditions suitable to provide a subsequent esterification reaction product including biodiesel, methanol, water and optionally free fatty acids;

(j) optionally repeating steps (h) and (i) one or more times, to provide an esterification reaction product including biodiesel;

wherein the methanol separated from the one or more esterification reaction products is purified to a purity of at least about 99.9 wt. %, and is employed in a subsequent esterification, transesterification, or combination thereof;

(k) contacting at a temperature of less than 102° F. (38.89° C.) (i) methanol, (ii) a solid heterogeneous transesterification catalyst, and (iii) the esterification reaction product, wherein the contacting is carried out under conditions suitable to provide a biodiesel, methanol, water, glycerin and optionally triglycerides;

(l) separating water, glycerin and methanol from the transesterification reaction product;

(m) contacting the transesterification reaction product with (i) methanol and (ii) a solid heterogeneous transesterification catalyst, wherein the contacting is carried out under conditions suitable to provide a subsequent transesterification reaction product including biodiesel, methanol, water, glycerin and optionally triglycerides; and (n) optionally repeating steps (l) and (m) one or more times, to provide a transesterification reaction product including biodiesel and glycerin;

wherein the methanol separated from the one or more transesterification reaction products is purified to a purity of at least about 99.9 wt. %, and is employed in a subsequent esterification, transesterification, or combination thereof;

(o) removing glycerin, water and methanol from the one or more transesterification reaction products, to provide a mixture including biodiesel;

(p) distilling the methanol obtained from the one or more transesterification reaction products, one or more times, to provide methanol having a purity of at least about 99 wt. %, and reusing the purified methanol in a subsequent esterification, transesterification, or combination thereof; and (q) distilling the biodiesel one or more times, to provide a purified biodiesel.

Production of Glycerin from Feedstock

The present invention also provides for the production of glycerin from feedstock. The process includes:

(a) filtering a biodiesel feedstock, thereby removing from the feedstock solid particles having a diameter up to 2 microns, to provide a filtrate and a retentate;

(b) separating at least one of moisture and water from the filtrate, to provide a dried filtrate;

(c) distilling the dried filtrate, to provide a distillate and a residue;

(d) distilling the distillate to provide a subsequent distillate and optionally a subsequent residue;

(e) optionally repeating steps (c) and (d), one or more times, by distilling the subsequent distillate, to obtain a final distillate;

(f) passing final distillate through an ion exchange resin;

(g) contacting (i) methanol, (ii) a solid heterogeneous esterification catalyst, and (iii) the final distillate, wherein the contacting is carried out under conditions suitable to provide an esterification reaction product including biodiesel, methanol, water, and optionally free fatty acids;

(h) separating water and methanol from the esterification reaction product;

(i) contacting the esterification reaction product with (i) methanol and (ii) a solid heterogeneous esterification catalyst, wherein the contacting is carried out under conditions suitable to provide a subsequent esterification reaction product including biodiesel, methanol, water and optionally free fatty acids;

(j) optionally repeating steps (h) and (i) one or more times, to provide an esterification reaction product including biodiesel;

wherein the methanol separated from the one or more esterification reaction products is purified to a purity of at least about 99.9 wt. %, and is employed in a subsequent esterification, transesterification, or combination thereof;

(k) contacting at a temperature of less than 102° F. (38.89° C.) (i) methanol, (ii) a solid heterogeneous transesterification catalyst, and (iii) the esterification reaction product, wherein the contacting is carried out under conditions suitable to provide a biodiesel, methanol, water, glycerin and optionally triglycerides;

(l) separating water, glycerin and methanol from the transesterification reaction product;

(m) contacting the transesterification reaction product with (i) methanol and (ii) a solid heterogeneous transesterification catalyst, wherein the contacting is carried out under conditions suitable to provide a subsequent transesterification reaction product including biodiesel, methanol, water, glycerin and optionally triglycerides; and (n) optionally repeating steps (l) and (m) one or more times, to provide a transesterification reaction product including biodiesel and glycerin;

wherein the methanol separated from the one or more transesterification reaction products is purified to a purity of at least about 99.9 wt. %, and is employed in a subsequent esterification, transesterification, or combination thereof;

(o) separating, via distillation, glycerin from the one or more transesterification reaction products; and (p) distilling the glycerin, and passing through activated carbon, to provide a purified glycerin.

Pretreatment, Esterification and Transesterification

The present invention also provides for the pretreatment, esterification and transesterification of biodiesel feedstock. The process includes:

(a) filtering a biodiesel feedstock, thereby separating from the feedstock solid particles having a diameter up to 2 microns, to provide a filtrate and a retentate;

(b) separating at least one of moisture and water from the filtrate, to provide a dried filtrate;

(c) distilling the dried filtrate, to provide a distillate and a residue;

(d) distilling the distillate to provide a subsequent distillate and optionally a subsequent residue;

(e) optionally repeating steps (c) and (d), one or more times, by distilling the subsequent distillate, to obtain a final distillate;

(f) passing final distillate through an ion exchange resin;

(g) contacting (i) methanol, (ii) a solid heterogeneous esterification catalyst, and (iii) the final distillate, wherein the contacting is carried out under conditions suitable to provide an esterification reaction product including biodiesel, methanol, water, and optionally free fatty acids;

(h) separating water and methanol from the esterification reaction product;

(i) contacting the esterification reaction product with (i) methanol and (ii) a solid heterogeneous esterification catalyst, wherein the contacting is carried out under conditions suitable to provide a subsequent esterification reaction product including biodiesel, methanol, water and optionally free fatty acids;

(j) optionally repeating steps (h) and (i) one or more times, to provide an esterification reaction product including biodiesel;

wherein the methanol separated from the one or more esterification reaction products is purified to a purity of at least about 99.9 wt. %, and is employed in a subsequent esterification, transesterification, or combination thereof;

(k) contacting at a temperature of less than 102° F. (38.89° C.) (i) methanol, (ii) a solid heterogeneous transesterification catalyst, and (iii) the esterification reaction product, wherein the contacting is carried out under conditions suitable to provide a biodiesel, methanol, water, glycerin and optionally triglycerides;

(l) separating water, glycerin and methanol from the transesterification reaction product;

(m) contacting the transesterification reaction product with (i) methanol and (ii) a solid heterogeneous transesterification catalyst, wherein the contacting is carried out under conditions suitable to provide a subsequent transesterification reaction product including biodiesel, methanol, water, glycerin and optionally triglycerides; and (n) optionally repeating steps (l) and (m) one or more times, to provide a transesterification reaction product including biodiesel and glycerin;

wherein the methanol separated from the one or more transesterification reaction products is purified to a purity of at least about 99.9 wt. %, and is employed in a subsequent esterification, transesterification, or combination thereof.

Advantages

In specific embodiments, advantages of the invention provide for a process for the production of biodiesel and/or glycerin that does not employ the introduction of water. In further specific embodiments, advantages of the invention provide for a pretreatment process that can employ a waterless wash process.

In specific embodiments, advantages of the invention provide for a process for the production of biodiesel and/or glycerin that does not employ the introduction of a toxic mineral acid (e.g., phosphoric acid, sulfuric acid, hydrochloric acid, citric acid, or a combination thereof). Specifically, the esterification process can be carried out in the absence of a toxic mineral acid. The use of acids often lead to strict regulations, disposal of waste, yield loss, incomplete removal of impurities (e.g., cannot always separate sulfur, polymerized triglycerides, dimmers, trimers and sterols), and additional safety measures.

For example, traditional sulfuric acid based esterification technologies can employ feedstock with a free fatty acid content of up to about 10-12 wt. %. In contrast, in specific embodiments of the present invention that do not employ the introduction of a toxic mineral acid, a feedstock with a free fatty acid content of up to 100 wt. % can be employed.

For example, traditional sulfuric acid based esterification technologies typically have yield below about 90 wt. %, due to incomplete conversion. In contrast, in specific embodiments of the present invention that do not employ the introduction of a toxic mineral acid, conversions of about 99.8 wt. %, and higher, are typically achieved.

In specific embodiments, advantages of the invention provide for a process that reuses reagent, in a safe and renewable manner. Specifically, each of the esterification and transesterification processes can independently reuse and purify the methanol, e.g., by distillation. This can lower the overall operating cost, lower the carbon footprint, and avoids the time and costs associated with any reagent disposal.

In specific embodiments, advantages of the invention provide for a process for the production of biodiesel and/or glycerin that emits little or no discharge into the atmosphere. Additionally, in specific embodiments, advantages of the invention provide for a process for the production of biodiesel and/or glycerin that does not include the generation of toxic waste, that would otherwise be disposed of, e.g., in a land-fill.

In specific embodiments, advantages of the invention provide for a process for the production of biodiesel and/or glycerin that are high-grade. In further specific embodiments, the biodiesel and/or glycerin produced from the methods described herein are products that meet or exceed stringent regulatory requirements (e.g., ASTM D6751 standards). For example, glycerin can be obtained in a 99.7% purity technical grade. In further specific embodiments, advantages of the invention provide for a process for the production of biodiesel and/or glycerin that include one or more impurities in the amounts illustrated in Table A. In further specific embodiments, advantages of the invention provide for a process for the production of biodiesel and/or glycerin that include each of the impurities in the amounts illustrated in Table A.

In specific embodiments, advantages of the invention provide for a process for the production of biodiesel and/or glycerin, wherein specific steps of the process are driven to completion (or near completion) by the removal or separation of side-product(s) from the crude reaction product, and subjecting the purified crude reaction product to that same process again. This respective process can be carried out until a minimal requisite amount of side-product is achieved.

For example, in an esterification process, biodiesel feedstock, catalyst, and methanol are subject to esterifying conditions, such that free fatty acids (FFA) present in the biodiesel feedstock are esterified, to produce a crude reaction product that includes biodiesel, water, methanol, triglycerides and unreacted free fatty acids. One way to assist in driving the esterification reaction to completion is carried out by removing or separating (e.g., via distillation) water and methanol (as a mixture) from the crude reaction product to provide a purified crude reaction product that includes biodiesel, triglycerides, and free fatty acids. This crude reaction product can be subject to esterifying conditions to convert at least a portion of the free fatty acids present therein to triglycerides. This repeated esterification process can be carried out until the amount of free fatty acids obtained in an esterifying process is below a requisite amount (e.g., below about 5 wt. %).

For example, in a transesterification process, biodiesel feedstock, catalyst, and methanol are subject to transesterifying conditions, such that triglycerides present in the biodiesel feedstock are transesterified, to produce a crude reaction product that includes biodiesel, water, glycerin, methanol, and unreacted triglycerides. One way to assist in driving the transesterification reaction to completion is carried out by removing or separating (e.g., via distillation) water, glycerin, and methanol (as a mixture) from the crude reaction product to provide a purified crude reaction product that includes biodiesel and triglycerides. This crude reaction product can be subject to transesterifying conditions to convert at least a portion of the triglycerides present therein to biodiesel. This repeated transesterification process can be carried out until the amount of triglycerides obtained in a transesterifying process is below a requisite amount (e.g., below about 5 wt. %).

In specific embodiments, advantages of the invention provide for a process for the production of biodiesel and/or glycerin, wherein specific steps of the process are driven to completion (or near completion) by employing a molar excess of reagent. For example, each of the transesterification and esterification processes can independently employ a molar excess of the reagent methanol.

In specific embodiments, advantages of the invention provide for a process for the production of biodiesel and/or glycerin, wherein a solid catalyst is employed in the esterification process, and free fatty acids are converted to triglycerides in yields of about 99.8%, and higher.

In specific embodiments, advantages of the invention provide for a process for the production of biodiesel and/or glycerin, wherein a solid catalyst is employed in the transesterification process, and triglycerides are converted to biodiesel in yields of about 99.8%, and higher.

In specific embodiments, advantages of the invention provide for a process for the production of biodiesel and/or glycerin, wherein a relatively wide-variety of inexpensive and low-grade feedstock can be employed, that would otherwise be considered waste and disposed of, e.g., in a land-fill. Such low-grade feedstock includes, e.g., brown grease, trap grease, and high free fatty acid based grease used cooking oil and animal fats, such as tallow, pork fat, poultry fat, lard, and choice white grease.

For example, in specific embodiments, advantages of the invention provide for a process for the production of biodiesel and/or glycerin, wherein the feedstock can include relatively high amounts of impurities (e.g., between about 15 ppm and 1000 ppm sulfur, up to 300 ppm phosphorus, up to 3 wt. % unsaponifiables and phospholipids, up to 0.5 wt. % polymerized triglycerides, up to 0.5% dimers and trimers, phytosterols, sitosterols, cholesterol, and/or sterol glucosides). In further specific embodiments, advantages of the invention provide for a process for the production of biodiesel and/or glycerin, that employs a low-grade biodiesel feedstock having one or more impurities in the amounts as illustrated in Table A herein. In further specific embodiments, advantages of the invention provide for a process for the production of biodiesel and/or glycerin, that employs a low-grade biodiesel feedstock having each of the impurities in the amounts as illustrated in Table A herein.

In specific embodiments, advantages of the invention provide for a process for the production of biodiesel and/or glycerin, wherein a biodiesel feedstock that includes up to about 100 wt. % free fatty acids (FFAs) can be employed.

In specific embodiments, advantages of the invention provide for a process for the production of biodiesel and/or glycerin in a relatively cost-effective manner, employing relatively low energy consumption. Specially, the transesterification process can be carried out at a temperature of about 95° F.

In specific embodiments, advantages of the invention provide for a process for the production of commercial or industrial amounts of biodiesel and/or glycerin (e.g., at least about 1,000 gallons) in a relatively short period of time (e.g., within about 48 hours).

In specific embodiments, advantages of the invention provide for a process for the production of biodiesel and/or glycerin, wherein any one or more of the steps of the production are carried out in a continuous fashion. In further specific embodiments, advantages of the invention provide for a process for the production of biodiesel and/or glycerin, wherein each of the steps of the production is carried out in a continuous fashion.

In specific embodiments, advantages of the invention provide for a process for the production of biodiesel and/or glycerin, wherein the production results in a relatively low carbon footprint.

In specific embodiments wherein the esterification employs a solid, heterogeneous esterification catalyst, advantages of the invention provide for a process that produces little or no soap. As such, any subsequent glycerin separation becomes relatively easier (in the absence of soaps and salts).

Traditional transesterification technologies sometimes employ sodium methylate, which leads to saponification issues, which in turn affects biodiesel-glycerin separation and lowers the glycerin purity, leading to a higher acid number and yield loss. Use of acids to neutralize and split he soaps typically leads to higher operating cost and disposal issues. Slower kinetics lead to larger footprint and restricts the use feedstocks higher in FFA, which are typically significantly less expensive than virgin oils. In contrast, in specific embodiments of the present invention that employ a solid, heterogeneous transesterification catalyst, advantages of the invention provide for a transesterification that can be carried out at lower temperatures (e.g., about 95° F.), the elimination of (or the ability to avoid the use of) sodium methylate, relatively short conversion times (e.g., 30-45 minutes retention time at each reactor stage), relatively high yields (e.g., above about 99 wt. % conversion of triglycerides to biodiesel and glycerin), the ability to employ a wide-range of biodiesel feedstocks, and/or with the ability to obtain the desired product (e.g., biodiesel and/or glycerin) in a relatively high yield (e.g., above about 99.5 wt. %) and high purity (e.g., above about 95 wt. %).

BRIEF DESCRIPTION OF THE DRAWINGS

Embodiments of the invention may be best understood by referring to the following description and accompanying drawings which illustrate such embodiments. The numbering scheme for the Figures included herein are such that the leading number for a given reference number in a Figure is associated with the number of the Figure. Reference numbers are the same for those elements that are the same across different Figures. For example, a process flow diagram depicting esterifying (206) can be located in FIG. 2. However, reference numbers are the same for those elements that are the same across different Figures. In the drawings:

FIG. 5 illustrates a process flow diagram for the esterification of free fatty acids.

FIG. 6 illustrates a process flow diagram for the transesterification of triglycerides.

DETAILED DESCRIPTION

Figure 1:
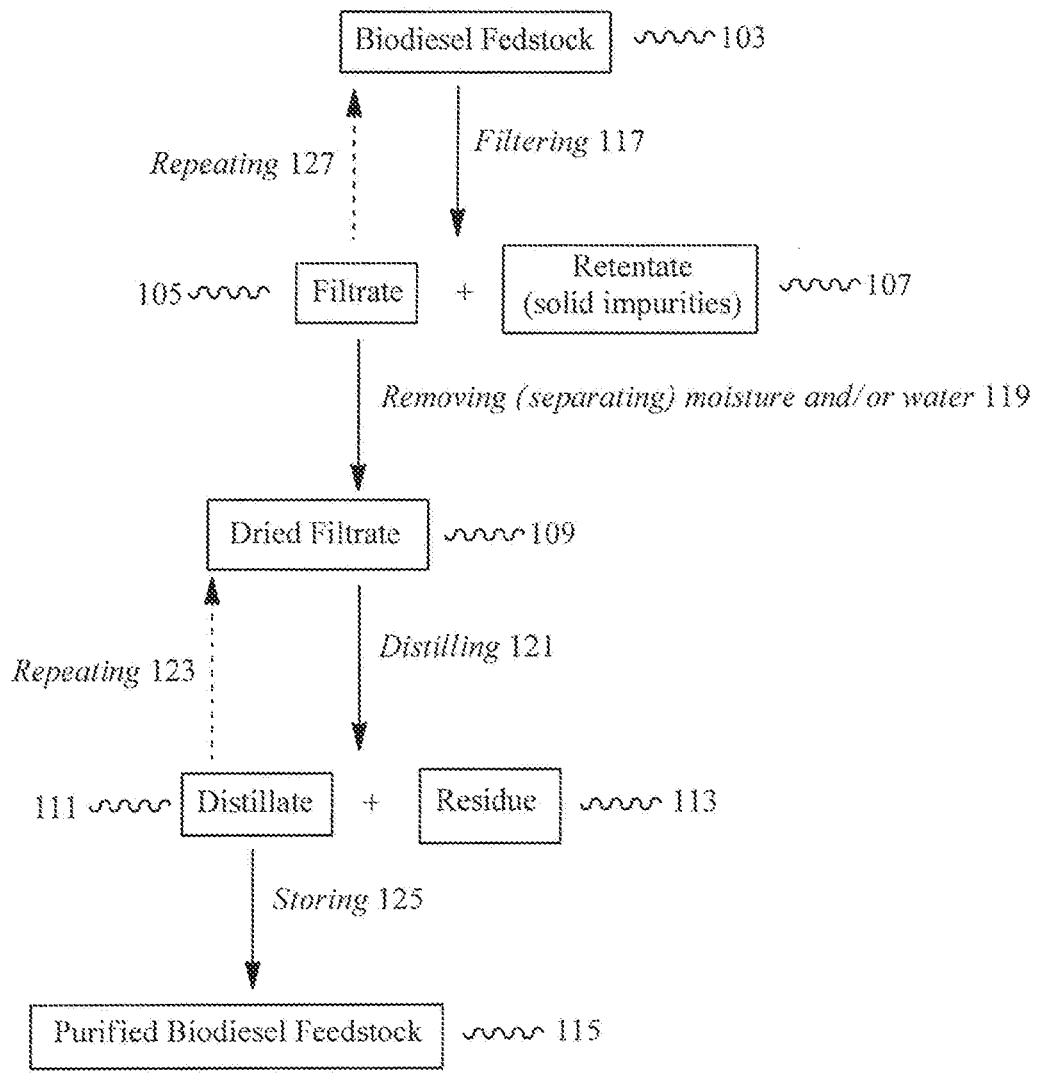
FIG. 1 illustrates a process flow diagram for the pretreatment of biodiesel feedstock.

The following detailed description includes embodiments and examples, in which the invention may be practiced. These embodiments and examples are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

Reference will now be made in detail to certain claims of the present invention, examples of which are illustrated herein. While the present invention will be described in conjunction with the enumerated claims, it will be understood that they are not intended to limit the claimed subject matter. On the contrary, the present invention is intended to cover all alternatives, modifications, and equivalents, which may be included within the scope of the present invention as defined by the claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The presently disclosed subject matter relates to methods for producing biodiesel and/or glycerin. When describing the methods for producing biodiesel and/or glycerin, the following terms have the following meanings, unless otherwise indicated.

DEFINITIONS

As used herein, "wt. %" refers to weight percent or weight percentage.

As used herein, "filtering" refers to a mechanical or physical operation which is used for the separation of solids from fluids (liquids or gases) by interposing a medium through which the fluid (and relatively small solid particles) can readily pass.

As used herein, "biodiesel feedstock" refers to those starting materials that are used to make biofuels. Biofuels are fuels derived from biological materials such as, e.g., plant oils and animal fats. Examples of "biodiesel feedstocks" are elaborated below in the section "Biodiesel Feedstocks." Typically, the biodiesel feedstock will include free fatty acids and triglycerides.

As used herein, "free fatty acids" refer to nonesterified fatty acids. Free fatty acids are sometimes present in biodiesel feedstock.

As used herein, "solid particles" refers to relatively small objects having a precise physical boundary in all directions. A particle is characterized by its volume and interfacial surface in contact with its environment. Solid particles have a definite shape.

As used herein, "diameter" refers to the maximum distance of a straight line that passes through the center of a particle and whose end points are on the surface of the particle.

As used herein, "filtrate" refers to the liquid produced after filtering a suspension of a solid in a liquid.

As used herein, "dried filtrate" refers to the removal or separation of moisture and/or water from the filtrate.

As used herein, "retentate" refers to the solid remaining in the filter after filtering a suspension of a solid in a liquid.

As used herein, "moisture" refers to the presence of a liquid, especially water, often in trace amounts. Moisture may be found, for example, in the air (humidity), in feedstock, and in various commercial products.

As used herein, "water" refers to a chemical substance with the chemical formula $H_2O$.

As used herein, "distilling" refers to a method of separating a mixture based on the difference in volatilities of components in a boiling liquid mixture.

As used herein, "distillate" refers to the concentrated or purified liquid, called the distillate that is collected as a result of distillation.

As used herein, "residue" refers to the portion of the mixture that remains after distillation and which is the least volatile material that has not been separately captured as a condensed vapor.

As used herein, "fats" refers to a wide group of compounds that are generally soluble in organic solvents and generally insoluble in water. Chemically, fats are triglycerides, triesters of glycerol and any of several fatty acids. Fats may be either solid or liquid at room temperature, depending on their structure and composition. Specifically, "fats" is usually used to refer to fats that are solids at normal room temperature As used herein, "oils" refer to fats that are liquids at normal room temperature, while "fats" is usually used to refer to fats that are solids at normal room temperature.

As used herein, "edible oils" refers to a liquid fat that is capable of being eaten as a food or food accessory.

As used herein, "inedible oils" refers to refers to a liquid fat that is not capable of being eaten as a food or food accessory.

As used herein, "grease" refers to soft or melted animal fat, especially after rendering.

As used herein, "brown grease" refers to waste vegetable oil, animal fat, grease, etc. that is recovered from a waste water component called a grease trap. It is the grease that is removed from wastewater sent down a sink drain. Brown grease is contaminated grease.

As used herein, "trap grease" refers to grease obtained from a plumbing devices designed to intercept most greases and solids before they enter a wastewater disposal system As used herein, "used cooking oil" refers to plant, animal, or synthetic cooking oil that has been previously used in frying, baking and other types of cooking.

As used herein, "used cooking fat" refers to plant, animal or synthetic fat that has been used in frying, baking, and other types of cooking As used herein, "animal fat" refers to solid lipid materials derived from animals. Chemically, animal fats are composed of triglycerides.

As used herein, "animal grease" refers to animal fat used or produced in cooking. It is often soft or melted.

As used herein, "fatty acid distillate" refers to the fatty acids obtained by distillation. Fatty acids generated during fat splitting or methyl esters from a transesterification process are generally purified by distillation to separate the fatty acids into groups according to their chain lengths.

As used herein, "tallow" refers to a rendered form of beef or mutton fat.

As used herein, "pork fat" refers to fat from a pig.

As used herein, "poultry fat" refers to fat obtained (usually as a by-product) from poultry rendering and processing.

As used herein, "lard" refers to pig fat in both its rendered and unrendered form.

As used herein, "choice white grease" refers to a specific grade of mostly pork fat defined by hardness, color, fatty acid content, moisture, insolubles, unsaponifiables, and free fatty acids.

As used herein, "algae oil" refers to the lipid or oily part of the algae biomass.

As used herein, "crude vegetable oils" refers to the unrefined and unprocessed oil produced from vegetables—and how it is found in the natural vegetable oil state when it is first extracted from the vegetable, whether the vegetable oil comes from corn, soybeans, oil palm, jatropha, cottonseed, etc. To make the crude vegetable oil ready for use, it must undergo further processing and refining to take it from its crude form to a "refined vegetable oil" state.

As used herein, "soybean oil" refers to a vegetable oil extracted from the seeds of the soybean (*Glycine max*).

As used herein, "corn oil" refers to oil extracted from the germ of corn (maize).

As used herein, "coffee oil" refers to a volatile, oily substance developed in the coffee bean upon roasting that gives coffee its essence.

As used herein, "hemp oil" or "hempseed oil" refers to the oil obtained by pressing hemp seeds. Hempseed oil is manufactured from varieties of *Cannabis sativa* that do not contain significant amounts of tetrahydrocannabinol (THC).

As used herein, "linseed oil" (also known as flaxseed oil) refers to colorless to yellowish oil obtained from the dried ripe seeds of the flax plant (*Linum usitatissimum*, Linaceae).

As used herein, "rice bran oil" (also known as rice bran extract) refers to the oil extracted from the germ and inner husk of rice.

As used herein, "jojoba oil" refers to the liquid wax produced in the seed of the jojoba (*Simmondsia chinensis*) plant.

As used herein, "tall oil" (also called "liquid rosin" or tallol) refers to a viscous yellow-black odorous liquid obtained as a by-product of the Kraft process of wood pulp manufacture when pulping mainly coniferous trees.

As used herein, "mustard oil" refers to any of three different oils that are made from mustard seeds: a fatty vegetable oil resulting from pressing the seeds; an essential oil resulting from grinding the seeds, mixing them with water, and extracting the resulting volatile oil by distillation; and an oil made by infusing mustard seed extract into another vegetable oil, such as soybean oil. The pungency of mustard oil is due to the presence of allyl isothiocyanate.

As used herein, "DDG" refers to non-starch components of the corn kernel that has undergone dewatering and dehydration. This by-product is sold as a commercial feed ingredient called DDG.

As used herein, "distillers grain oil" or "DDG corn oil" refers to the corn oil that is present in DGG. It can be obtained by extraction from DGG.

As used herein, "*Jatropha* oil" refers to the oil obtained from the crushed seeds of *Jatropha* plants. *Jatropha* is a genus of flowering plants in the spurge family, Euphorbiaceae.

As used herein, "camellia oil" (also known as tea oil, camellia oil, or tsubaki oil) refers to an edible, pale amber-green fixed oil with a sweet, herbal aroma. It is cold-pressed mainly from the seeds of *Camellia oleifera* but also from *Camellia sinensis, Camellia japonica* and *Camellia sasanqua*.

As used herein, "rapeseed oil" also known as rape, oilseed rape, rapa, rappi, rapeseed) and, in the case of one particular group of cultivars, canola, refers to the oil derived from the seeds of the rapeseed plant, members of the family Brassicaceae.

As used herein, "canola oil" refers to the oil derived from the seeds of a cultivar of either Rapeseed (*Brassica napus* L.) or field mustard (*Brassica campestris* L. or *Brassica Rapa* var.).

As used herein, "moringa oil" (also known as Ben oil) refers to the oil obtained by pressing the seeds of the Moringa Oilefera Tree.

As used herein, "pongamia oil" refers to the oil derived from the seeds of the *Millettia pinnata* tree. *Millettia pinnata*, also known as Pongamia glabra, is common throughout Asia and thus has many different names in different languages, many of which have come to be used in English to describe the seed oil derived from *M. pinnata*; Honge is the Kannada word for this tree. Other names for this oil include Karanja oil (from Hindi), Pungai oil (from Tamil), Honge oil (from the Kannada word for the tree), and Pongamia oil.

As used herein, "sunflower oil" refers to the non-volatile oil compressed from sunflower (*Helianthus annuus*) seeds As used herein, "safflower oil" refers to a vegetable oil extracted from the seeds of the safflower plant (*Carthamus tinctorius* L).

As used herein, "crude palm oil" refers to the pre-purified oil that is extracted from the palm nut kernel. It contains non-glyceride components such as trace metals, kernel shell pieces and products of oxidation. Purification removes or separates these components and makes the palm oil edible and sellable.

As used herein, "palm kernel oil" refers to an edible plant oil derived from the kernel of the oil palm *Elaeis guineensis*. It is a highly saturated vegetable fat containing the 16-carbon saturated fatty acid palmitic acid.

As used herein, "palm fatty acid distillate" refers to a by-product of the crude palm oil refinery plant. The main components of Palm Fatty Acid Distillate (PFAD) are the free fatty acids, oleic, stearic, and palmitic.

As used herein, "palm sludge oil" refers to the fibers remaining after the palm fruit has been pressed to extract all the oil. It is also called "the slurry."

As used herein, "coconut oil" refers to an edible oil extracted from the kernel or meat of matured coconuts harvested from the coconut palm (*Cocos nucifera*).

As used herein, "filter" refers to a material that has very tiny holes and is used to separate out solid particles contained in a liquid or gas that is passed through it. It also refers to the action of passing a material through a filter.

As used herein, "multiple" refers to comprising, consisting of, including, containing, or involving more than one.

As used herein, "porosity" refers to the property of a material having many pores or other small spaces that can hold a gas or liquid or allow it to pass through.

As used herein, "mesh size" refers to is the number of openings per linear inch of mesh. Mesh materials are often used to determine the particle size distribution of a granular material or to separate or filter out particles by size. One well-known mesh series is the Tyler Equivalent created by the W.S. Tyler screening company. Tyler mesh size is the number of openings per (linear) inch of mesh. The higher mesh number the small the spaces between the mesh wires.

As used herein, "recycling" refers to the processing of reusing excess starting material, excess solvent, and/or excess reagent that is recovered, e.g., in a reaction product. For example, in each of the esterification and transesterification reactions described herein, methanol is employed as a reagent. When present in a stoichiometric excess (e.g., 1.25 molar equivalent), methanol will typically be present in the reaction product. This methanol can be separated from the reaction product, isolated and purified. The purified methanol can then be reused (or recycled) in a subsequent esterification and/or transesterification reaction. The recycling of materials (e.g., methanol), can lower the use of toxic chemicals, can prevent the waste of potentially useful materials, can reduce the consumption of fresh raw materials, can reduce energy usage, can reduce air pollution (from incineration) and water pollution (from land filling) by reducing the need for "conventional" waste disposal, and/or can lower greenhouse gas emissions as compared to virgin production.

As used herein, "reflux ratio" refers to the ratio of parts condensate returned to heating flask to parts condensate taken off to the collection flask when separating two compounds by distillation.

As used herein, "non-toxic" refers to a material that is not poisonous, harmful, or otherwise destructive to an organism upon exposure.

As used herein, "continuously" refers to an event that is uninterrupted in time; without cessation.

As used herein, "continuously distilling" refers to form of distillation. It is an ongoing separation in which a mixture is continuously (without interruption) fed into the process and separated fractions are removed continuously as output streams.

As used herein, "single stage distillation column" refers to a type of distillation in which only one stage is provided in which liquids boil and vapors condense. Single stage columns are often used to provide coarse separation of components with widely different boiling points.

As used herein, "multi-stage distillation column" refers to a type of distillation column in which successive stages are provided in which liquids boil and the vapors from the stage above condense and in which equilibrium between the two streams, liquid and vapor, is attained.

As used herein, "vacuum," refers to a region of space having extremely low gas pressure relative to surrounding pressure.

As used herein, "in vacuum," or "under vacuum" refers to an extremely low gas pressure, relative to surrounding pressure.

As used herein, "qualitative nature of impurities" refers to the kinds of impurities present.

As used herein, "quantitative nature of impurities" refers to the amount of impurities present.

As used herein, "adsorbent" refers to a material on which on which atoms or molecules move from a bulk phase (that is, solid, liquid, or gas) onto a solid or liquid surface (the adsorbant). An example is purification by adsorption where impurities are filtered from liquids or gases by their adsorption onto the surface of a high-surface-area solid such as activated charcoal. Ambersep™ BD19 purification resin is an example of an exchange resin that is an adsorbant."

As used herein, "separated" or "separating" refers to the isolation of at least one material from a mixture of materials, or the setting or keeping apart of materials.

As used herein, "purifying" refers to the process of removing or separating impurities from a material.

As used herein, "subsequently distilled" refers to distilling a material after first performing or treating a material in a prescribed manner.

As used herein, "subsequent distillate" refers to the concentrated or purified liquid (i.e., distillate) obtained by redistilling a previous distillate.

As used herein, "residue" refers to the portion of the mixture that remains after distillation and which is the least volatile residue that has not been separately captured as a condensed vapor.

As used herein, "subsequent residue" refers to the portion of the mixture that remains (i.e., the residue) that remains after redistilling a previous distillate.

As used herein, "stored" or "storing" refers to placing or leaving a material in a location for preservation, later use, or disposal.

As used herein, "contacting" refers to placing two materials together or touching, such as objects or surfaces.

As used herein, "methanol" refers to the compound $CH_3OH$. Methanol is also known as methyl alcohol, wood alcohol, wood naphtha or wood spirits.

As used herein, "solid heterogeneous catalyst" refers to a catalyst that is in a different phase than the reactants. For example the catalyst may be a solid and the reactants may be a liquid. Amberlyst™ BD20 is an example of a heterogeneous esterification catalyst.

As used herein, "esterifying" refers to the process of forming an ester. This process typically involves treating a carboxylic acid with an alcohol in the presence of a dehydrating agent. An esterification reaction is shown below.

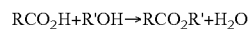

$$RCO_2H + R'OH \rightarrow RCO_2R' + H_2O$$

When the biodiesel feedstock includes free fatty acids, those free fatty acids can be esterified (e.g., with methanol and esterification catalyst, under suitable conditions), to provide biodiesel as the desired product, and water as the by-product.

As used herein, "toxic mineral acid" refers to a mineral acid that is poisonous, harmful, corrosive, or otherwise destructive to an organism upon exposure. Mineral acids are inorganic acids derived from one or more inorganic compounds. All mineral acids form hydrogen ions and the conjugate base ions when dissolved in water. Examples of toxic mineral acids are sulfuric acid, nitric acid, hydrochloric, and nitric acid.

As used herein, "phosphoric acid" also known as orthophosphoric acid or phosphoric (V) acid, refers to a mineral (inorganic) acid having the chemical formula $H_3PO_4$.

As used herein, "sulfuric acid" refers to a highly corrosive strong mineral acid with the molecular formula $H_2SO_4$.

As used herein, "hydrochloric acid" refers to a clear colorless solution of hydrogen chloride (HCl) in water. It is a highly corrosive, strong mineral acid.

As used herein, "citric acid" refers to a weak organic acid having the formula:

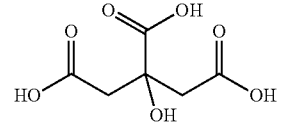 [SMILES: O=C(O)CC(O)(CC(=O)O)C(=O)O]

As used herein, "conversion" refers to the action of a chemical reaction, e.g. the conversion of molecule A to molecule B. Examples include the conversion of free fatty acids to their methyl ester.

As used herein, "soap" refers to the salt of a fatty acid.

As used herein, "salt product" refers to ionic compounds produced that result from the neutralization reaction of an acid and a base. Examples include the sodium salts of fatty acids.

As used herein, "by-product" refers to a material produced usually in an industrial or biological process in addition to the principal product.

As used herein, "side-product" refers to a product from a manufacturing process that is not considered the principal material, e.g., is the minor product.

As used herein, "standard temperature" refers to 273.15° K (0° Celsius).

As used herein, "standard pressure" refers to 1 atm pressure.

As used herein "standard ambient temperature and pressure" refers to 293.15° K (25° Celsius) and 1 atm pressure.

As used herein, "premixed" refers to materials that are mixed or blended from two or more ingredients or elements before being marketed, used, or mixed further.

As used herein, "ion exchange resin" or "ion exchange polymer" refers to an insoluble matrix (or support structure) normally in the form of small (e.g., 1-2 mm diameter) beads, usually white or yellowish, fabricated from an organic polymer substrate. Ion exchange resins have a highly developed structure of pores on the surface of which are sites with easily trapped and released ions. The trapping of ions takes place only with simultaneous releasing of other ions; thus the process is called ion-exchange. There are multiple different types of ion-exchange resin which are fabricated to selectively prefer one or several different types of ions.

As used herein, "Ambersep™ BD19" refers to an ion exchange resin that includes specific inert polymer beads and adsorbent. The ion exchange resin can effectively remove or separate unwanted components from high fatty acid feedstocks, prior to esterification, and can improve the operability of the downstream biodiesel production process. The Ambersep™ BD19 purification technology can replace traditional oil degumming processes. The ion exchange resin can be employed in the pretreatment process, to extend the life of the Amberlyst™ BD20 esterification catalyst (employed in the subsequent esterification process). Even the smallest traces of soap, catalyst, and glycerol should be removed from crude biodiesel in order to meet stringent new international quality specifications. The ion exchange resin improves operability of downstream manufacturing processes by removing or separating chemical and physical foulants (e.g., cations, proteins, phospholipids, etc.). The ion exchange resin also helps prevent potential side reactions caused by unwanted components. The Ambersep™ BD19 ion exchange resin is commercially available from Rohm and Haas Company (Philadelphia, Pa.).

As used herein, "straight, flow-through 2 stage guard bed column reactor in series" refers to the use for example of two catalyst beds, one after the other. In the first stage, the first bed, known as the guard bed, contains a low-cost catalyst to remove or react with most of the impurities. In the second stage, a second more expensive bed is used to remove or separate the remaining impurities.

As used herein, "Amberlyst™ BD20 solid catalyst" refers to a solid, heterogeneous polymeric esterification catalyst, for the conversion of high free fatty acid (FFA) feedstock materials into valuable biodiesel. The solid catalyst is useful with, e.g., crude vegetable oils, animal fats, greases, fatty acid distillate, and recycled materials with an FFA range from 0.5 to 100%. Use of the solid catalyst can lower feedstock cost, increase process flexibility, increase biodiesel and/or glycerin yield, and improves biodiesel and/or glycerin purity. Amberlyst™ BD20 solid, heterogeneous catalyst is commercially available from Dow Chemical (Midland, Mich.).

As used herein, "stoichiometric excess" refers to an excess of at least one reagent or reactant over that which is the optimum amount of reagents to completely form the product. A stoichiometric excess of a reagent can be used to drive a reaction to completion.

As used herein, "molar excess" refers to an excess in the molar amount of at least one reagent or reactant over the number of moles of the optimum moles of reagents to completely form the product.

As used herein, "flash column" refers to a distillation column used in flash vaporization. Flash vaporization is a process in which a continuous liquid-mixture feed stream is partly vaporized in a column or vessel, with continuous withdrawal of vapor and liquid portions, the vapor and liquid in equilibrium. It is also known as continuous equilibrium vaporization; equilibrium distillation; flash distillation; and simple continuous distillation.

As used herein, "demister pads" refers to devices a fitted to vapor liquid separator vessels to enhance the removal of liquid droplets entrained in a vapor stream. Demisters may be a mesh type coalescer, vane pack or other structure intended to aggregate the mist into droplets that are heavy enough to separate from the vapor stream.

As used herein, "un-reacted" refers to the portion of starting materials in a chemical reaction that do not combine.

As used herein, "subsequent" refers to something later in time or order than something else. Synonyms are following, and succeeding.

As used herein, "first stage reactor" refers to a reactor or vessel in which an initial reaction or processing occurs. For example, with an esterification, some of the free fatty acids and methanol is converted to biodiesel and water in a $1^{st}$ stage esterification reactor.

As used herein, "second stage reactor" refers to a reactor or vessel in which a reaction (or processing) takes place (or occurs) for a second time. For example, with an esterification, some of the free fatty acids and methanol is converted to biodiesel and water in a $2^{nd}$ stage esterification reactor.

As used herein, "third stage reactor" refers to a reactor or vessel in which a reaction (or processing) takes place (or occurs) for a third time. For example, with an esterification, some of the free fatty acids and methanol is converted to biodiesel and water in a $3^{rd}$ stage esterification reactor.

As used herein, "triglycerides" refers to an ester formed from a molecule of glycerol and three molecules of fatty acids. The structure of a triglyceride is shown below.

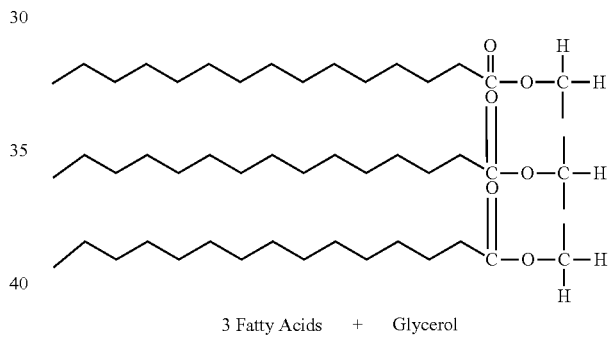

3 Fatty Acids + Glycerol

As used herein, "crude reaction product" refers to the product of a reaction that is initially obtained, prior to a purification step.

As used herein, "immobilized on a solid support" refers to any technique in which reagents are bound (i.e., immobilized or insolubilized) on a support, to prevent them from being removed during use.

As used herein, "continuous" refers to refers to an event that is uninterrupted in time; without cessation.

As used herein, "batch mode" refers to a manufacturing process in which materials are fed into the manufacturing process in batches, and the product is produced in batches. It differs from "continuous mode" where starting materials are continuously fed into the manufacturing process and product is continuously produced.

As used herein, "repeat," "repeated," or "repeating" refers to doing something or performing an operation the same way, substantially the same way, or in an equivalent manner as previously done.

As used herein, "glycerin" refers to propane-1,2,3-triol. It has the structure shown below.

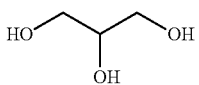

As used herein, "transesterifying" refers to the process of exchanging the organic group $R_1$ of an ester with the organic group $R_2$ of an alcohol (shown below as the methyl group of methanol). Transesterification is the main reaction for converting transglycerides in oil to biodiesel. The transesterification process includes the reaction of an alcohol (such as methanol) with the triglyceride oils contained in vegetable oils, animal fats, or recycled greases, forming fatty acid alkyl esters (biodiesel) and glycerin. The reaction typically requires heat and a strong base catalyst, such as sodium hydroxide or potassium hydroxide. With respect to biodiesel, a transesterification reaction is shown below.

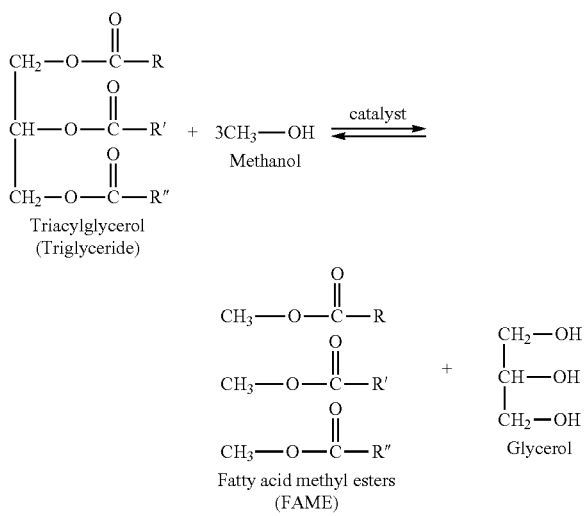

As such, the transesterification is typically represented by: alcohol+ester→different alcohol+different ester.

As used herein, "Biocatalyst A solid catalyst" refers to a methanol-resistant enzyme biocatalyst developed by Trans-Biodiesel (Israel) that is capable of esterifying/transesterifying oil components and short-chain alcohols to form biodiesel.

As used herein, "enzyme biocatalyst" refers to an immobilized enzyme, typically used for the production of biodiesel. The "biocatalyst" is multifunctional it converts a wide-range grade of vegetable oil and animal fat to biodiesel with minimal waste products. The enzymes are typically biodegradable and safe to human use. Enzymes are proteins that increase (biologically catalyze) the rates of chemical reactions and therefore are called sometimes "biocatalysts." Enzyme activity can be affected by other molecules (inhibitors) such as methanol or ethanol. Inhibitors are molecules that decrease enzyme activity; while activators such as Free Fatty Acid are molecules that increase activity. The enzymes are immobilized in order to protect them from a direct contact with the inhibitors. The enzymes are lipase derived.

As used herein, "degrade" refers to making something worse in quality or performance; to lower the purity of a material, typically occurring when the desired compound is converted to an undesired compound.

As used herein, "sodium methylate" refers to sodium methoxide, a chemical compound, with formula $CH_3ONa$.

As used herein, "optionally" refers to a step, process or method that is either carried out, or is not carried out.

As used herein, "sterols" refers to a subgroup of steroids with a hydroxyl group at the 3-position of the A-ring. This hydroxyl group is often esterified with a fatty acid (for example, cholesterol ester). The hydrocarbon chain of the fatty-acid substituent varies in length, usually from 16 to 20 carbon atoms, and can be saturated or unsaturated. Sterols commonly contain one or more double bonds in the ring structure and also a variety of substituents attached to the rings. Sterols and their fatty-acid esters are essentially water insoluble. They occur naturally in plants, animals, and fungi, with the most familiar type of animal sterol being cholesterol.

As used herein, "monoglycerides" (more correctly known as monoacylglycerols) refers to a glyceride consisting of one fatty acid chain covalently bonded to a glycerol molecule through an ester linkage. Monoacylglycerides can be broadly divided into two groups; 1-monoacylglycerides and 2-monoacylglycerides, depending on the position of the ester bond on the glycerol moiety.

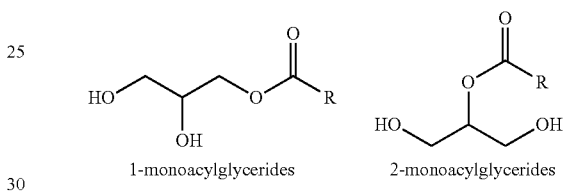

As used herein, "diglycerides" refers to a glyceride consisting of two fatty acid chains covalently bonded to a glycerol molecule through ester linkages.

As used herein, "triglycerides" refers to a glyceride consisting of three fatty acid chains covalently bonded to a glycerol molecule through ester linkages.

As used herein, "convert," "converted," or "converting" refers to changing (something) into another form, substance, state, or product; to transform. For example, the biocatalyst converts a wide-range grade of vegetable oil and animal fat to biodiesel, with minimal waste products.

As used herein, "acid number" refers to the mass of potassium hydroxide (KOH) in milligrams that is required to neutralize one gram of chemical substance. The acid number is a measure of the amount of carboxylic acid groups in a chemical compound, such as a fatty acid.

As used herein, "flash point" refers to the lowest temperature at which a volatile material can vaporize to form an ignitable mixture in air.

As used herein, "moisture content" refers to the quantity of water contained in a material.

As used herein, "sulfur content" refers to the amount of sulfur in a material.

As used herein, "phosphorus content" refers to the amount of phosphorous in a material.

As used herein, "content of polymerized triglycerides" refers to the amount of polymerized triglycerides present in a sample of biodiesel feedstock. Polymerized triglycerides are formed, for example, from fryer grease during heating at high temperature for a period of time.

As used herein, "sterols content" refers to the quantity of sterols in a material, particularly in a plant, an, animal, or a fungus.

As used herein, "activated carbon" also called activated charcoal, activated coal, or carbo activatus, refers to a form of carbon processed to be riddled with small, low-volume pores that increase the surface area available for adsorption or chemical reactions.

As used herein, "pure" refers to a material that is not mixed with any appreciable or significant amount of other materials, e.g., that is not contaminated in any substantial way. For example, a pure substance can have a purity of at least 99 wt. %, at least 99.5 wt. %, or at least 99.9 wt. %.

In specific embodiments, steps of a process that are carried out are indicated by a solid-lined arrow (see, FIGS. 1-6). Alternatively, in specific embodiments, steps of a process that are optionally carried out are indicated by a dashed-lined arrow (see, FIGS. 1-6). It is appreciated that those of skill in the art of biodiesel production understand and appreciate that for convenience and brevity purposes, such optional steps may be described as affirmatively being carried out, but that such steps, however, are optional and as such, are not necessarily carried out.

Pretreatment of Biodiesel Feedstock

The pretreatment process is employed to ensure as reasonably feasible the quality, yield, and downstream operational efficiency in the biodiesel refining process. This process removes or separates solid particles, sulfur, phosphorus, phosphatides, gums, sterols, metals and/or other color bodies from the feedstock.

Pretreatment of fats, oils and grease-based feedstocks can be carried out with a continuous distillation process. In a continuous process, time that the feedstock remains in the column is relatively short, and hence the degree of polymerization is reduced.

The maximum permissible temperature is typically dependent upon how much the oils polymerize under the specific conditions. Under the pretreatment process, pre-filtered, dried and homogenized feed oil enters a heat exchanger (re boiler) using hot oil as thermic fluid, where it is heated to process temp of about 200-230° C. Feed then gets flashed from the re-boiler and enters the column from the bottom and flows upward, which operates under vacuum of about 27 inches of Hg. The column containing structured packing. The high volatile components in the vapor state flow upwards to the top of the column. Less volatile components (e.g., color bodies, metals, sterols, sulfur, gums etc.) remain in the bottom of the column.

The overhead vapors, which include mainly triglycerides and free fatty acids, are recycled with a reflux ratio of 1-1.5 to further maximize the purity to about 99.95 wt. %. After the desired purity is achieved, the vapors are condensed using chiller. The clean oil is further sent to a holding tank, which is now ready for the transesterification and/or the esterification. The bottoms include polymerized oil that contains sulfur, phosphorus, chlorophyll, phosphatides, gums, sterols and metals like calcium, magnesium, iron, copper, sodium and potassium.

Figure 4:
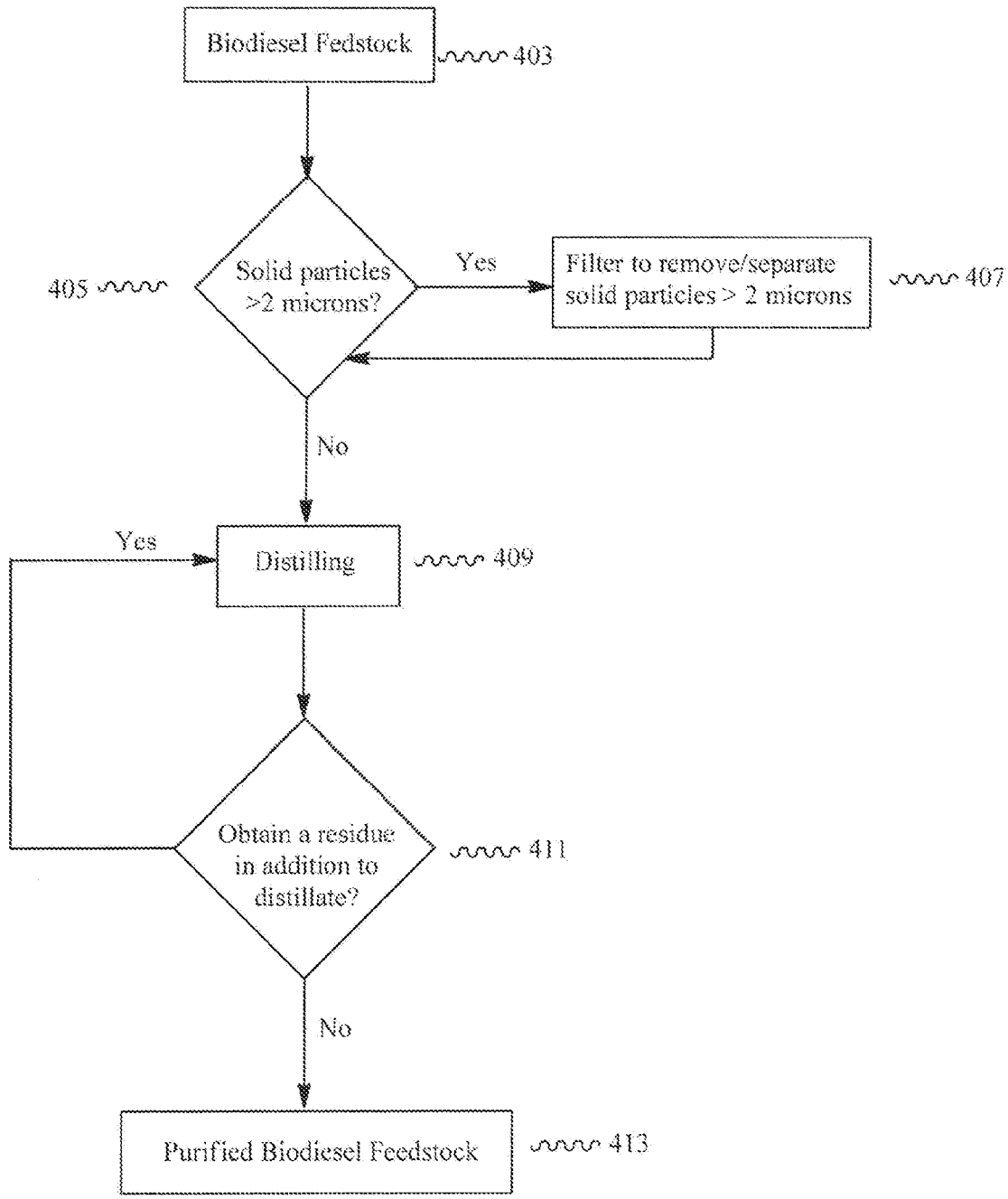
FIG. 4 illustrates a process flow diagram for the pretreatment of biodiesel feedstock.

Referring to FIG. 4, a process flow diagram is provided for the pretreatment of biodiesel feedstock (401). Briefly stated, if a biodiesel feedstock (403) includes solid particles greater than 2 microns (405), the biodiesel feedstock (403) is filtered (407), to remove or separate the solid particles greater than 2 microns. The filtering (407) of biodiesel feedstock (403) is carried out (e.g., repeated) until the biodiesel feedstock (403) does not include a significant or appreciable amount of solid particles greater than 2 microns (405). The biodiesel feedstock (403) that does not include a significant or appreciable amount of solid particles greater than 2 microns (405) is distilled (409). The distillation (409) is carried out to provide a distillate and residue (411). The distillate (411) is distilled (409) to provide a subsequent distillate (411) and subsequent residue (411). The distillation is carried out (e.g., repeated) until no significant or appreciable amount of residue (411) is obtained. Once no significant or appreciable amount of residue (411) is obtained from the one or more distillations (409), the one or more distillates (411) are combined and stored (not shown), to provide a purified biodiesel feedstock (413).

Referring to FIG. 1, a process flow diagram is provided for the pretreatment of biodiesel feedstock (101). Briefly stated, a biodiesel feedstock (103) is filtered (117) to provide a filtrate (105) and retentate (107). The filtering (117) can be repeated (127) one or more times. The retentate (107) is non-toxic, and can safely be disposed, e.g., in a land fill. Water and/or moisture are removed or separated (119) from the filtrate (105), to provide a dried filtrate (109). The dried filtrate (109) is distilled (121), to provide a distillate (111) and residue (113). The distillate (111) and residue (113) can be separated. The distillate (111) itself is distilled (121), i.e., the process is repeated (123), such that the distilling (121), to provide distillate (111) and residue (113), is carried out, wherein the distillate (111) itself is subsequently distilled (121). The distilling (121) of the distillate (111) can be repeated (123) one or more times, to provide a subsequent distillate (111) and subsequent residue (113). The process is repeated (123), one or more times. Each of the residues (113) is non-toxic and can safely be disposed, e.g., in a land fill. Finally, the distillate (111) is stored (125), to provide a purified biodiesel feedstock (115).

Each step of the pretreatment of biodiesel feedstock (101) can independently be carried out in a continuous fashion, or in a batch mode.

Biodiesel Feedstock

The pretreatment (and any subsequent processes) can be carried out employing a wide-range of biodiesel feedstocks (103). For example, the biodiesel feedstocks (103) can include at least one of fats, oils, and grease.

Specifically, the biodiesel feedstocks (103) can include at least one of edible oils, inedible oils, fats, greases, oils produced from microbial/biological/biotechnology/fermentation/metabolic activity, or similar-based process, brown grease, trap grease, used cooking oil, used cooking fat, animal fat, animal grease, and fatty acid distillate.

Specifically, the biodiesel feedstocks (103) can include at least one of tallow, pork fat, poultry fat, lard, choice white grease, algae oil, crude vegetable oils, soybean oil, corn oil, coffee oil, hemp oil, linseed oil, rice bran oil, jojoba oil, tall oil, mustard oil, distillers grain oil (DDG corn oil), *Jatropha* oil, camellia oil, rapeseed oil, canola oil, moring a oil, pongamia oil, sunflower oil, safflower oil, crude palm oil, palm kernel oil, palm fatty acid distillate, palm sludge oil, coconut oil, and their derivatives (including genetically modified and otherwise).

The biodiesel feedstocks (103) will typically include a significant and appreciable amount of free fatty acids. In specific embodiments, the biodiesel feedstocks (103) includes up to about 100 wt. % free fatty acids. In specific embodiments, the biodiesel feedstocks (103) includes about 0.2 wt. % to about 100 wt. % free fatty acids. In specific embodiments, the biodiesel feedstocks (103) includes about 1 wt. % to about 99 wt. % free fatty acids. In specific embodiments, the biodiesel feedstocks (103) includes about 5 wt. % to about 99 wt. % free fatty acids.

Filtering

The biodiesel feedstock (103) is filtered (117), to provide a filtrate (105) and retentate (107). The filtrate (105) will typically pass through the filter, as the retentate (107) is retained by the filter. The filtering (117) can be repeated (127) one or more times. As such, the biodiesel feedstock (103) can be filtered (117) one or more times, to provide a filtrate (105) and one or more retentates (107). In specific embodiments, the repeating (127) is carried out until there is little or no appreciable and significant amount of retentate (107). When the biodiesel feedstock (103) is filtered (117) multiple times, the porosity or mesh size will typically vary from filter to filter. For example, the initial filtering (117) can be carried out with a filter having relatively larger openings (i.e., a lower Tyler mesh size, which is the number of openings per linear inch of mesh). With each subsequent filtering (117), a filter can be employed having relatively smaller openings (i.e., a higher Tyler mesh size). The filtering (117) can be carried out such that relatively larger-sized solid particles are removed or separated in the initial filtering (117). With each subsequent filtering (117), progressively smaller-sized solid particles are removed or separated.

When the biodiesel feedstock (103) is filtered (117) multiple times as described herein, smaller-sized solid particles can effectively and efficiently be removed or separated from the biodiesel feedstock (103), on an industrial or commercial scale. Additionally, smaller-sized solid particles can effectively and efficiently be removed or separated from the biodiesel feedstock (103) with a decreased likelihood that larger-sized solid particles will interfere with (e.g., clog or gum-up) the filter having relatively smaller openings (i.e., a higher Tyler mesh size). In specific embodiments, the final filtering (117) is carried out employing a filter having a requisite mesh size, such that solid particles having a diameter up to 2 microns are effectively removed or separated.

Specifically, the one or more filterings (117) can be carried out, such that at least about 50 wt. % of the solid particles having a diameter up to 2 microns are effectively removed or separated. More specifically, the one or more filterings (117) can be carried out, such that at least about 75 wt. % of the solid particles having a diameter up to 2 microns are effectively removed or separated. More specifically, the one or more filterings (117) can be carried out, such that at least about 85 wt. % of the solid particles having a diameter up to 2 microns are effectively removed or separated. More specifically, the one or more filterings (117) can be carried out, such that at least about 90 wt. % of the solid particles having a diameter up to 2 microns are effectively removed or separated. More specifically, the one or more filterings (117) can be carried out, such that up to about 100 wt. % of the solid particles having a diameter up to 2 microns are effectively removed or separated.

The biodiesel feedstock (103) can be filtered (117) one time, or multiple times. For example, the biodiesel feedstock (103) can be filtered (117) about 1-25 times, about 1-15 times, about 1-10 times, or about 1-5 times. Specifically, the biodiesel feedstock (103) can be filtered (117) at least about 2 times, at least about 3 times, at least about 4 times, or at least about 5 times.

In specific embodiments, the filtering (117) is carried out in a batch mode. Alternatively, in specific embodiments, the filtering (117) is carried out in a continuous fashion. In specific embodiments, the filtering (117) is continuous, and can include a single filter. In alternative specific embodiments, the filtering (117) is continuous, and can include multiple filters, as described herein.

The filtering (117) of the biodiesel feedstock (101) can be carried out on a commercial or industrial scale. For example, at least about 100 gallons of biodiesel feedstock (101) can be filtered (117). Specifically, within about 24 hours, at least about 100 gallons of biodiesel feedstock (101) can be filtered (117). Additionally, at least about 1,000 gallons of biodiesel feedstock (101) can be filtered (117). Specifically, within about 24 hours, at least about 1,000 gallons of biodiesel feedstock (101) can be filtered (117).

Removing Moisture and/or Water

Water and/or moisture can be removed or separated (119) from the filtrate (105), to provide a dried filtrate (109). The moisture can be removed by employing distillation and/or evaporators, in single or multi-stages, with or without vacuum. Moisture and/or water can be present in the feedstock from about 0.1 wt. % to about 99.5 wt. %, with final oil stream having about 1 wt. % or less moisture in it, typically about 500-2000 ppm. As such, in specific embodiments of the invention, the removing moisture and/or water can occur (e.g., can be carried out) during the one or more distillings (121).

Distilling

The dried filtrate (109) is distilled (121), to provide a distillate (111) and residue (113). The dried filtrate (109) is distilled (121) under suitable conditions, effective to provide the distillate (111) and residue (113). For example, the distilling (121) can be carried out at elevated temperatures and/or reduced pressures (e.g., under vacuum). Specifically, the distilling (121) can be carried out at elevated temperatures, e.g., at about 100° C. to about 530° C. Specifically, the distilling (121) can be carried out at reduced pressures, e.g., about 24 to about 29.92 inches of mercury (Hg).

The distilling (121) can be repeated (123) one or more times. As such, the dried filtrate (109) can be distilled (121), to provide distillate (111) and residue (113), wherein the distillate (111) is distilled (121) providing yet a subsequent distillate (111), and optionally a subsequent residue (113). In specific embodiments, the repeating (123) is carried out until there is little or no appreciable and significant amount of residue (113). In more specific embodiments, the repeating (123) is carried out until less than about 5 wt. % residue (113) is obtained, relative to the biodiesel feedstock (101). In more specific embodiments, the repeating (123) is carried out until less than about 1 wt. % residue (113) is obtained, relative to the biodiesel feedstock (101). In more specific embodiments, the repeating (123) is carried out until less than about 0.5 wt. % residue (113) is obtained, relative to the biodiesel feedstock (101).

The dried filtrate (109) and/or distillate (111) can be distilled (121) one time, or multiple times. For example, the dried filtrate (109) and/or distillate (111) can be distilled (121) about 1-25 times, about 1-15 times, about 1-10 times, or about 1-5 times. Specifically, the dried filtrate (109) and/or distillate (111) can be distilled (121) at least about 2 times, at least about 3 times, at least about 4 times, or at least about 5 times.

In specific embodiments, the dried filtrate (109) and/or distillate (111) are distilled (121) multiple times, such that the residue (113) is about 0.1% to about 10% the weight of the dried filtrate (109) and/or distillate (111). In further specific embodiments, the dried filtrate (109) and/or distillate (111) are distilled (121) multiple times, such that the residue (113) is about 0.2% to about 6% the weight of the dried filtrate (109) and/or distillate (111).

In specific embodiments, the distilling (121) is carried out in a batch mode. Alternatively, in specific embodiments, the distilling (121) is carried out in a continuous fashion. In specific embodiments, the distilling (121) is continuous, and can include a single stage distillation column. In alternative specific embodiments, the distilling (121) is continuous, and can include a multi-stage distillation column. Additionally, the single stage (or multi stage) distillation column can operate with or without vacuum.

The distilling (121) can be carried out on a commercial or industrial scale. For example, the distilling (121) can be carried out to provide at least about 100 gallons of distillate (111). Specifically, the distilling (121) can be carried out to provide, within about 24 hours, at least about 100 gallons of distillate (111). Additionally, the distilling (121) can be carried out to provide at least about 1,000 gallons of distillate (111). Specifically, the distilling (121) can be carried out to provide, within about 24 hours, at least about 1,000 gallons of distillate (111).

The one or more distillings (121) are carried out to increase the purity level of the distillate (111). This can be accomplished, e.g., by removing, separating, or lowering the amount of the one or more impurities located therein. When impurities are removed or separated via distillation (121), the residue (113) will be enriched in those impurities, relative to the distillate (111).

In specific embodiments, the one or more distillings (121) are carried out to provide distillate (111) and residue (113), such that relative to the distillate (111), the residue (113) is enriched in at least one of sulfur, phosphorus, gums/lipids, sterols, calcium, magnesium, iron, copper, cobalt, manganese, nickel, sodium, potassium, chlorophyll, carotenoids, xanthophylls, proteins and carbohydrates, aldehydes, ketones, carboxylic acids, perchloroethylene, polyaromatic hydrocarbons, polychlorinated hydrocarbons, polymerized triglycerides, pesticides, soaps, detergents, sulfonates, sulfates, phosphatides, phytosterols, sitosterols, cholesterol, sterol glucosides, oils and fats, other trace impurities, and other colored bodies.

In specific embodiments, the one or more distillings (121) are carried out to provide distillate (111) and residue (113), such that relative to the residue (113), the distillate (111) is enriched in at least one of triglycerides and free fatty acids.

The distillate (111) will typically include an appreciable and significant amount of at least one of triglycerides and free fatty acids. In specific embodiments, the distillate (111) includes up to about 95 wt. % of at least one of triglycerides and free fatty acids. In further specific embodiments, the distillate (111) includes up to about 99 wt. % of at least one of triglycerides and free fatty acids. In further specific embodiments, the distillate (111) includes up to about 99.5 wt. % of at least one of triglycerides and free fatty acids. In further specific embodiments, the distillate (111) includes up to about 99.995 wt. % of at least one of triglycerides and free fatty acids.

In specific embodiments, the distillate (111) includes at least one of triglycerides and free fatty acids, wherein the at least one of triglycerides and free fatty acids combined include less than about 7 ppm phosphorus, less than about 7 ppm sulfur, and less than about 10 ppm of all other metals combined. In further specific embodiments, the distillate (111) includes at least one of triglycerides and free fatty acids, wherein the at least one of triglycerides and free fatty acids combined include less than about 7 ppm sulfur.

Storing

The distillate (111) is stored (125), to provide a purified biodiesel feedstock (115). The distillate (111) can be stored (125), e.g., in a suitable manner, in a suitable vessel, under suitable conditions, and for a suitable period of time, to provide a purified biodiesel feedstock (115).

Specifically, the distillate (111) can be stored (125) at about ambient temperature and pressure. Alternatively, the distillate (111) can be stored (125) below room temperature. Alternatively, the distillate (111) can be stored (125) at a temperature of about 0° C. to about 60° C., at a temperature of about 5° C. to about 50° C., at a temperature of about 10° C. to about 40° C., or at a temperature of about 10° C. to about 30° C.

The distillate (111) can be stored (125) for a suitable period of time. For example, the distillate (111) can be stored (125) for up to about 6 months, up to about 1 month, up to about 1 week, or up to about 24 hours. Specifically, the distillate (111) can be stored (125) for about 1 minute to about 48 hours, about 10 minutes to about 48 hours, or about 1 hour to about 24 hours.

Impurities Present in Biodiesel Feedstock

The pretreatment of biodiesel feedstock (101) can be carried out to increase the purity level of the biodiesel feedstock (101). As such, in specific embodiments, the pretreatment of biodiesel feedstock (101) is a method of purifying a biodiesel feedstock (101). This method of purification can be accomplished, e.g., by removing, separating, or lowering the amount of the one or more impurities located therein. Suitable impurities typically present in biodiesel feedstock (101) include, e.g., those illustrated in Table A herein, in the amounts illustrated therein.

In specific embodiments, the biodiesel feedstock (101), prior to the pretreatment process, is analyzed to determine the qualitative nature of impurities located therein. In specific embodiments, the biodiesel feedstock (101), prior to the pretreatment process, is analyzed to determine the quantitative nature of impurities located therein.

In specific embodiments, the biodiesel feedstock (101) includes at least one of triglycerides, gums, soaps, detergents, unsaponifiables, phosphatides, metals, phosphorus, sulfur, sulfates, sulfonates, sulfides, polyaromatic hydrocarbons, polychlorinated hydrocarbons, polyethylene, plant based sterols, animal based sterols, moisture, and water.

In specific embodiments, the biodiesel feedstock (101) includes elevated levels of at least one of water, sulfur, phosphorus, gums/lipids, sterols, calcium, magnesium, iron, copper, cobalt, manganese, nickel, sodium, potassium, chlorophyll, carotenoids, xanthophylls, proteins and carbohydrates, aldehydes, ketones, carboxylic acids, perchloroethylene, polyaromatic hydrocarbons, polychlorinated hydrocarbons, polymerized triglycerides, pesticides, soaps, detergents, sulfonates, sulfates, phosphatides, phytosterols, sitosterols, cholesterol, sterol glucosides, and other colored bodies.

In specific embodiments, the biodiesel feedstock (101) includes up to about 20,000 ppm of at least one of sulfur, sulfates, sulfides, and sulfonates.

In specific embodiments, the biodiesel feedstock (101) includes up to about 4000 ppmw phosphorus.

In specific embodiments, the pretreatment of biodiesel feedstock (101) is carried out to remove or separate from the feedstock (101) at least one of water, sulfur, phosphorus, gums, strerols, calcium, magnesium, iron, copper, sodium, potassium, chlorophyll, phosphatides, and colored bodies.

In specific embodiments, the pretreatment of biodiesel feedstock (101) is carried out to remove or separate at least one of water, sulfur, phosphorus, gums/lipids, sterols, calcium, magnesium, iron, copper, cobalt, manganese, nickel, sodium, potassium, chlorophyll, carotenoids, xanthophylls, proteins and carbohydrates, aldehydes, ketones, carboxylic acids, perchloroethylene, polyaromatic hydrocarbons, polychlorinated hydrocarbons, polymerized triglycerides, pesticides, soaps, detergents, sulfonates, sulfates, phosphatides, phytosterols, sitosterols, cholesterol, sterol glucosides, oils and fats, other trace impurities, and other colored bodies.

Esterification of Free Fatty Acids

As described herein, an esterification is the general name for a chemical reaction in which two reactants (typically an alcohol and an acid) form a carboxylic ester as the desired reaction product, and water as the side-product. With reference to Biodiesel, free fatty acids (present in the feedstock) react with the reagent methanol in presence of catalyst (optionally at an elevated temperature and/or pressure) to form biodiesel and water.

Employing an ion exchange resin and a solid, heterogeneous esterification catalyst, the esterification process described herein can process feedstock containing up to 100% FFAs (multi-feedstocks), in 3 stages, with an 99.8 wt. % or higher conversion. The esterification catalyst can last about 6-9 months, and not only lowers the feedstock costs but also improves the biodiesel and glycerin quality significantly without the use of toxic acids and chemicals. Because of the heterogeneous catalyst, no soap is produced in this process and biodiesel-glycerin separation (in absence of soaps and salts) becomes relatively easier.

The esterification described can effectively convert any feedstock, even at very high FFA content. Other catalysts typically suffer from incomplete conversion, resulting in yield loss and saponification in the downstream transesterification unit. The fast kinetics of the solid heterogeneous esterification catalyst described herein allow for rapid throughput, whereas other esterification processes may limit production by creating a bottleneck in the process.

The dried and clean feedstock from the pretreatment unit passes through a guard bed with ion exchange resin, which filters any trace elements or components like gums/metals that can poison the solid heterogeneous esterification catalyst. It consists of a straight flow through 2 stage guard bed column in series (lead-lag) with no application of heat or pressure.

The feedstock is premixed with methanol using a shear mixer and then heated to operating parameters of about 185° F. and about 30 psi. Being an equilibrium reaction, molar flow rate of methanol is about 100% in excess of the stoichiometric requirements, with respect to the free fatty acid content of the feedstock entering into the $1^{st}$ stage reactor. The feedstock enters the reactor from the top and uniformly flows downward with the aid of a distributor. The reactor is a packed bed column with the solid heterogeneous esterification catalyst that includes screens at the top and bottom to hold the catalyst in a given area based on the optimization parameters like L/D ratio, Diameter of the column, etc. Residence time (about 30-45 minutes) combined with temperature, pressure, molar flow rates, fluid dynamics and column design helps achieve excellent conversion (about 90% approx.), yields and operating efficiencies.

To maximize the conversion of free fatty acids into biodiesel, water which acts as a rate limiting agent, is removed or separated between the reactor stages to drive the reaction to completion. Upon conversion, the $1^{st}$ stage reactor bottoms are sent to a flash still (operating under vacuum of about 26 Inches Hg, with a temperature of about 195° F.), where excess water and methanol are removed or separated.

The water-methanol stream from overheads of this and subsequent flash stills are sent to methanol distillation column (atmospheric pressure, 146° F.), where the methanol is purified to about 99.80% purity. Bottoms of the flash still which include biodiesel, triglycerides and unconverted FFAs, are sent to $2^{nd}$ stage reactor where relatively pure methanol is mixed (100% molar excess, with respect to the FFA content) and the whole stream is heated to process temperature of about 185° F. and introduced into the $2^{nd}$ stage reactor.

The output of the $2^{nd}$ stage reactor is typically a stream containing less than 1% FFA with a mix of biodiesel and triglycerides, along with excess methanol and water formed from the reaction. The stream is sent to $2^{nd}$ stage flash still where methanol and water is flashed off.

Bottoms of the $2^{nd}$ stage flash still, which include triglycerides, biodiesel and less than 1 wt. % FFA are sent to a final $3^{rd}$ stage reactor, which operates similarly to the first and second stage reactors with respect to flow rates, temp, pressure and design of the column. The resulting triglyceride and biodiesel stream from the $3^{rd}$ stage reactor has moisture and methanol content less than about 0.2% which proceeds to the transesterification process.

Water/methanol flashed from the flash stills is sent to methanol distillation column, which purifies methanol to about 99.70 wt. % purity. The purified and recovered methanol is used (recycled) in the esterification process (or transesterification process).

Referring to FIG. 5, a process flow diagram is provided for the esterification of free fatty acids (503), present in biodiesel feedstock. Briefly stated, the biodiesel feedstock (503) is pretreated with an ion exchange resin, to provide a treated biodiesel feedstock (507). The free fatty acids present in the treated biodiesel feedstock (507) are then esterified. Specifically, the treated biodiesel feedstock (507) is contacted (509) with an esterifying reagent and catalyst, to provide an esterification mixture (511). The esterification mixture (511) includes the treated biodiesel feedstock (507), which in turn includes the free fatty acids. The esterification mixture (511) also includes methanol (as the esterifying reagent) and a solid, heterogeneous esterification catalyst. The esterification mixture (511) is subject to esterification conditions (515), such that the free fatty acids present therein are esterified, to provide an esterification reaction product (517) that includes biodiesel as the desired product and water as a by-product. When a stoichiometric excess (e.g., 1.25 molar equivalent) of methanol is employed in the esterification (e.g., 509 and 511), the esterification reaction product (517) will also typically include unreacted methanol (517). The esterification reaction product (517) is separated, to provide biodiesel (523), and a mixture (521) of methanol and water.

If the biodiesel (523) contains a significant and appreciable amount of unreacted free fatty acids (533), the biodiesel (523) is contacted (509) with an esterifying reagent and catalyst, to provide a subsequent esterification mixture (511). The subsequent esterification mixture (511) is subject to esterification conditions (515), such that the free fatty acids present therein are esterified, to provide a subsequent esterification reaction product (517) that includes biodiesel as the desired product and water as a by-product. Again, when a stoichiometric excess of methanol is employed in the subsequent esterification (e.g., 509 and 511), the subsequent esterification reaction product (517) will also typically include unreacted methanol (517). The subsequent esterification reaction product (517) is separated, to provide a subsequent biodiesel (523), and a subsequent mixture (521) of methanol and water.

The esterification is carried out (e.g., repeated) until no significant or appreciable amount of free fatty acids (533) is obtained. Once no significant or appreciable amount of free fatty acids (533) is obtained in the biodiesel (523) is used as biodiesel feedstock (539).

The mixture (521) of methanol and water is separated (527) to provide methanol (529) and water (531). The methanol (529) is purified via distillation (535) to provide purified methanol (537). The purified methanol (537) can be reused (513) in a subsequent esterification reaction and/or transesterification reaction.

Figure 2:
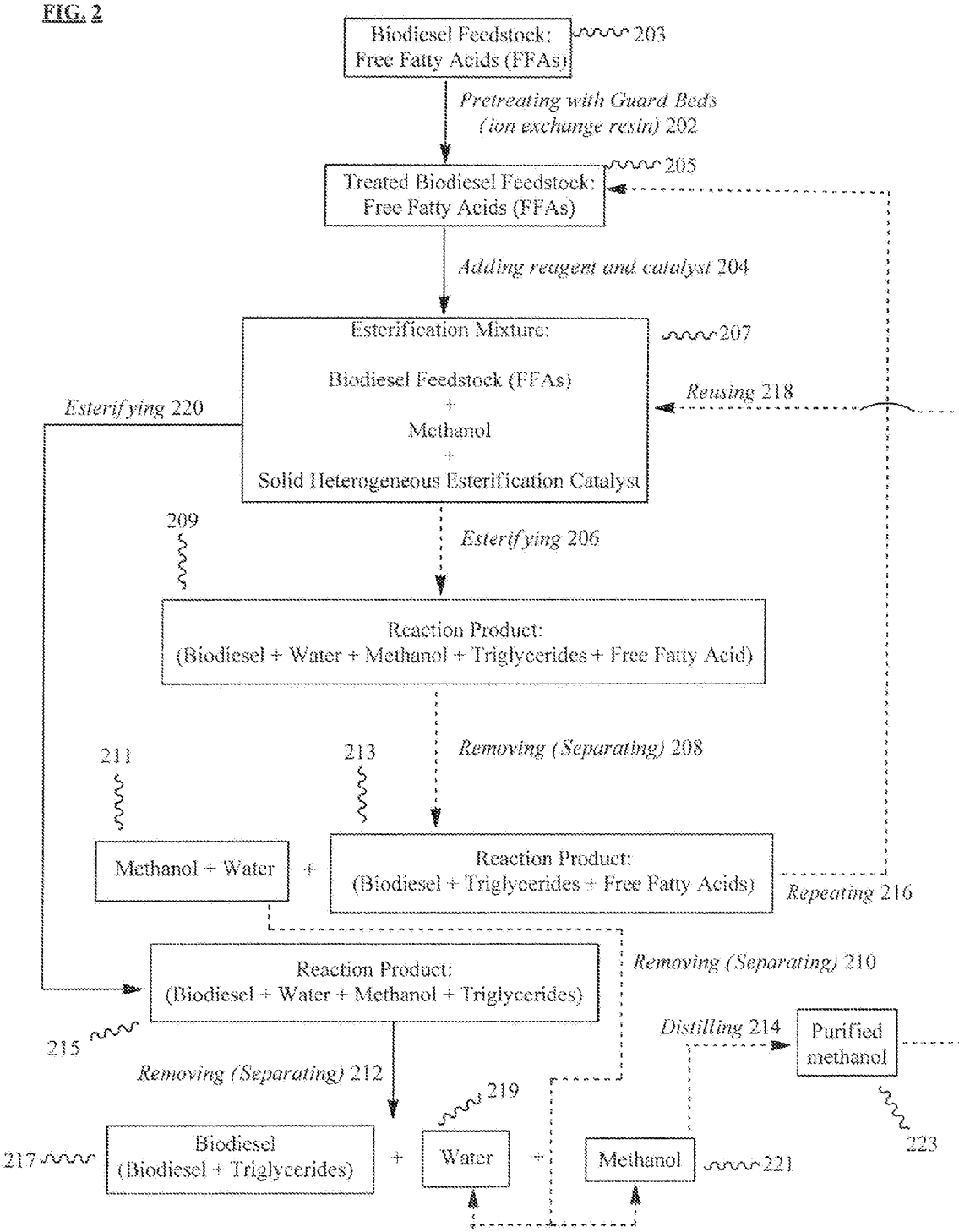
FIG. 2 illustrates a process flow diagram for the esterification of free fatty acids.

Referring to FIG. 2, a process flow diagram is provided for the esterification of free fatty acids (201), present in biodiesel feedstock. The biodiesel feedstock (203) can include purified biodiesel feedstock (115) obtained in the pretreatment of biodiesel feedstock (not shown, see FIG. 1). Briefly stated, a biodiesel feedstock (203) is pretreated (202) with guard bed column reactors (that includes an ion exchange resin, such as, e.g., Ambersep™ BD19 purification resin), to provide a treated biodiesel feedstock (205). The treated biodiesel feedstock (205) is contacted with an esterifying reagent and catalyst (204), such as methanol and a solid heterogeneous catalyst. The mixture (207) of biodiesel feedstock, methanol, and solid heterogeneous catalyst is subject to esterification conditions (220), to provide a reaction product (215) that includes biodiesel, water, methanol, and triglycerides. The reaction product (215) is separated (212), to provide biodiesel (217), water (219), and methanol (221). The methanol (221) is distilled off (214), to provide purified methanol (223). The purified methanol (223) is reused (218) to form a mixture (207), which is esterified (220 or 206).

The mixture (207) is subject to esterification conditions (206), to provide a reaction product (209). The reaction product (209) is separated, to provide a mixture (211) and reaction product (213). The reaction product (213) contacts (204) reagent and catalyst, to provide mixture (217), which is subjected to esterifying conditions (206), to provide reaction product (209). Reaction product (209) undergoes a separation (208), to provide mixture (211) and reaction product (213). The process is repeated (216), one or more times, until the final esterifying (220) provides reaction product (215).

Each step of the esterification of free fatty acids (201) can independently be carried out in a continuous fashion, or in a batch mode.

Pretreating with Guard Bed Column Reactors

Biodiesel feedstock (203) is pretreated (202) with guard bed column reactors, to provide a treated biodiesel feedstock (205). The pretreatment (202) is carried out to remove or separate at least one of trace elements, impurities and foulants selected from gums, metals, cations, proteins, and phospholipids. As such, relative to the treated biodiesel feedstock (205), the biodiesel feedstock (203) has elevated levels of at least one of trace elements, impurities and foulants selected from gums, metals, cations, proteins, and phospholipids.

In specific embodiments, prior to the pretreating (202), the biodiesel feedstock (203) is premixed with methanol. In alternative specific embodiments, prior to the pretreating (202), the biodiesel feedstock (203) is not premixed with methanol.

In specific embodiments, the biodiesel feedstock (203) is pretreated (202) at standard temperature. In alternative specific embodiments, the biodiesel feedstock (203) is pretreated (202) at an elevated temperature.

In specific embodiments, the biodiesel feedstock (203) is pretreated (202) at standard pressure. In alternative specific embodiments, the biodiesel feedstock (203) is pretreated (202) at an elevated pressure.

In specific embodiments, the biodiesel feedstock (203) is pretreated (202) by passing through an Ambersep™ BD19 purification resin. In more specific embodiments, the biodiesel feedstock (203) is pretreated (202) with an Ambersep™ BD19 purification resin, which consists of a straight, flow-through 2 stage guard bed column reactors in series.

Esterifying

Mixture (207) that includes biodiesel feedstock, methanol, and solid heterogeneous esterification catalyst is subject to esterification (220 or 206) conditions. The biodiesel feedstock (203), the treated biodiesel feedstock (205), and the biodiesel feedstock present in mixture (207) each include free fatty acids. These free fatty acids present in biodiesel feedstock are esterified with the methanol, with the aid of the solid heterogeneous catalyst.

Mixture (207) is subject to esterification (220 or 206) conditions, to provide reaction product (215) that includes biodiesel, water, methanol, and triglycerides. Alternatively, mixture (207) is subject to esterification (220 or 206) conditions, to provide reaction product (209) that includes biodiesel, water, methanol, triglycerides, and free fatty acids. When mixture (207) is subject to esterification (220 or 206) conditions, to provide reaction product (209), mixture (211) that includes methanol and water is separated (208) from the reaction product (209), to provide reaction product (213) that includes biodiesel, triglycerides, and free fatty acids. Reaction product (213) is subsequently contacted (204) with reagent and catalyst, to form mixture (207), which is subject to esterification conditions (206). This process (esterification (206) and separation (208)) is optionally repeated (216) one or more times, until the final esterifying (220) substantially provides reaction product (215).

The esterifying (220 or 206) can be carried out under suitable esterification conditions. Typically, the esterification (220 or 206) can be carried out at an elevated temperature. In specific embodiments, the methanol, catalyst, and biodiesel feedstock are heated to a temperature of at least about 170° F. (76.67° C.). In further specific embodiments, the methanol, catalyst, and biodiesel feedstock are heated to a temperature of up to about 200° F. (93.33° C.). In further specific embodiments, the methanol, catalyst, and biodiesel feedstock are heated to a temperature of between about 170° F. (76.67° C.) to about 200° F. (93.33° C.).

The esterifying (220 or 206) can be carried out at an elevated pressure. In specific embodiments, the methanol, catalyst, and biodiesel feedstock are heated at a pressure of at least about 15 psi (1.02 atm). In further specific embodiments, the methanol, catalyst, and biodiesel feedstock are heated at a pressure of up to about 50 psi (3.40 atm).

The esterifying (220 or 206) is carried out for a requisite period of time. In specific embodiments, the methanol, catalyst, and biodiesel feedstock are heated for a period of time of at least about 15 minutes. In further specific embodiments, the methanol, catalyst, and biodiesel feedstock are heated for a period of time of up to about 75 minutes. In further specific embodiments, the methanol, catalyst, and biodiesel feedstock are heated for a period of time of about 15 minutes to about 75 minutes.

When the esterifying (220 or 206) is carried out on a commercial or industrial scale, the reagent can be employed in a molar or stoichiometric excess. This will assist in driving the reaction to completion. This is especially so when the esterifying (206) and separating (208) are carried out one or more times, thereby removing or separating water from each of the one or more reaction products. With the esterifying (220 or 206) described herein, the methanol can be employed in a molar or stoichiometric excess, relative to the free fatty acid content of the biodiesel feedstock.

In specific embodiments, the methanol is employed in at least a 5 molar or stoichiometric excess, relative to the free fatty acid content of the biodiesel feedstock. In further specific embodiments, the methanol is employed in at least a 10 molar or stoichiometric excess, relative to the free fatty acid content of the biodiesel feedstock. In further specific embodiments, the methanol is employed in at least a 20 molar or stoichiometric excess, relative to the free fatty acid content of the biodiesel feedstock. In further specific embodiments, the methanol is employed in up to a 100 molar or stoichiometric excess, relative to the free fatty acid content of the biodiesel feedstock.

The esterifying (220 or 206) provides a reaction product (215 or 209) that aside from water, includes relatively few by-products. For example, in specific embodiments, the esterifying (220 or 206) provides a reaction product (215 or 209) that includes little or no (e.g., less than about 0.5 wt. %) soap product. In specific embodiments, the esterifying (220 or 206) provides a reaction product (215 or 209) that includes little or no (e.g., less than about 0.5 wt. %) salt product. In specific embodiments, the esterifying (220 or 206) provides a reaction product (215 or 209) that includes little or no (e.g., less than about 0.5 wt. %) by-products.

The esterifying (220 or 206) employs methanol as the reagent, present in mixture (207). The methanol will have a requisite purity. For example, in specific embodiments, the methanol will have a purity of at least about 99 wt. %, at least about 99.5 wt. %, at least about 99.9 wt. %, or at least about 99.95 wt. %. In further specific embodiments, the methanol will have a purity of up to about 100 wt. %. Employing methanol having a requisite purity, within the esterifying (220 or 206), will assist in driving the esterification (220 or 206) to completion, while providing a relatively high yield and/or purity of desired product.

The esterifying (220 or 206) employs a solid heterogeneous catalyst, present in the mixture (207). In specific embodiments, the solid heterogeneous catalyst includes Amberlyst™ BD20 solid catalyst (Rohm and Haas). In specific embodiments, the solid heterogeneous catalyst is immobilized on a solid support. In specific embodiments, the solid heterogeneous catalyst is non-toxic and is suitable for safely disposal in a land fill. It is believed that by employing a purified biodiesel feedstock (115) as the biodiesel feedstock (203), the commercial life of the solid heterogeneous catalyst will be extended. This can lower the actual cost of the solid heterogeneous catalyst, as well as the labor costs and cost of down-time associated with replacing the solid heterogeneous catalyst.

In specific embodiments, the solid heterogeneous catalyst is active in the esterification (220 or 206) for at least about 6 months. In further specific embodiments, the solid heterogeneous catalyst is active in the esterification (220 or 206) for at least about 12 months. In further specific embodiments, the solid heterogeneous catalyst is active in the esterification (220 or 206) for up to about 18 months.

The esterifying (206) can be repeated (216) one or more times. As such, the mixture (207) can be subjected to esterification (206) conditions, to provide reaction product (209), which can be separated into mixture (211) and reaction product (213). Reaction product (213) can subsequently be contacted (204) with reagent and catalyst, to form mixture (207), which can be subjected to esterification (206) conditions.

The esterifying (220) is carried out one time. Additionally, the esterifying (206) is carried out zero or more times. When carried out two or more times, the esterifying (206) is repeated (216) zero or more times and the esterifying (220) is carried out one time. In specific embodiments, the esterifying (206) is carried out about 0-25 times, about 1-15 times, about 1-10 times, or about 1-5 times. In more specific embodiments, the esterifying (206) is carried out at least about 1 time, at least about 2 times, or at least about 3 times.

In specific embodiments, the repeating (216) is carried out until the final esterifying (220) substantially provides reaction product (215). In more specific embodiments, the repeating (216) is carried out until the final esterifying (220) substantially provides reaction product (215), that includes little or no (e.g., less than about 5 wt. %) free fatty acids. In further specific embodiments, the repeating (216) is carried out until the final esterifying (220) provides reaction product (215), that includes less than about 1 wt. % free fatty acids. In further specific embodiments, the repeating (216) is carried out until the final esterifying (220) provides reaction product (215), that includes less than about 0.5 wt. % free fatty acids. In further specific embodiments, the repeating (216) is carried out until the final esterifying (220) provides reaction product (215), that includes less than about 0.1 wt. % free fatty acids.

In specific embodiments, the esterifying (220 or 206) is carried out in a batch mode. Alternatively, in specific embodiments, the esterifying (220 or 206) is carried out in a continuous fashion.

In specific embodiments, the esterifying (220 or 206) is continuous, and can include a single stage reactor. In alternative specific embodiments, the esterifying (220 or 206) is continuous, and can include a multi-stage reactor (e.g., first stage reactor, second stage reactor and third stage reactor). A multi-stage reactor is a reference to esterifying (220) and one or more esterifyings (206), in FIG. 2.

When a multi-stage reactor is employed, each stage independently provides for the conversion of free fatty acids and methanol to biodiesel and water. In specific embodiments, each stage provides a conversion of at least about 80 wt. % of free fatty acids present therein, to biodiesel and water. In more specific embodiments, each stage provides a conversion of at least about 90 wt. % of free fatty acids present therein, to biodiesel and water. In further specific embodiments, each stage provides a conversion of at least about 95 wt. % of free fatty acids present therein, to biodiesel and water. Additionally, the single stage (or multi stage) reactor can be configured to operate at elevated temperature and/or at elevated pressure.

The esterifying (220 or 206) can independently be carried out on a commercial or industrial scale. For example, the esterifying (220 and 206) can be carried out to provide at least about 100 gallons of combined reaction product (209 and 215). Specifically, the esterifying (220 and 206) can be carried out to provide, within about 24 hours, at least about 100 gallons of combined reaction product (209 and 215). Additionally, the esterifying (220 and 206) can be carried out to provide at least about 1,000 gallons of combined reaction product (209 and 215). Specifically, the esterifying (220 and 206) can be carried out to provide, within about 24 hours, at least about 1,000 gallons of combined reaction product (209 and 215).

When the esterifying (220 or 206) is carried out as described herein, the free fatty acids are esterified with methanol, with a relatively high conversion. In specific embodiments, the free fatty acids are esterified with methanol, with a combined conversion of at least about 70 wt. %. In further specific embodiments, the free fatty acids are esterified with methanol, with a combined conversion of at least about 85 wt. %. In further specific embodiments, the free fatty acids are esterified with methanol, with a combined conversion of at least about 95 wt. %. In further specific embodiments, the free fatty acids are esterified with methanol, with a combined conversion of at least about 98 wt. %. In further specific embodiments, the free fatty acids are esterified with methanol, with a combined conversion of at least about 99 wt. %. In further specific embodiments, the free fatty acids are esterified with methanol, with a combined conversion of up to about 100 wt. %.

Separating/Distilling

Each of the reaction product (209), mixture (211), and reaction product (215) can be separated (208, 210, and 212, respectively). For example, the reaction product (209) can be separated (208) to provide a mixture (211) of methanol and water, and reaction product (213) that includes biodiesel, triglycerides, and free fatty acids. The mixture (211) can be separated (210) to provide water (219) and methanol (221). The reaction product (215) can be separated (210) to provide biodiesel (217) that includes biodiesel and triglycerides, along with water (219), and methanol (221). Each of the separations can independently be carried out, e.g., by employing distillation. Additionally, the methanol (221) can be distilled (214) to provide purified methanol (223).

Each of the distillations in the esterification of free fatty acids (201) can independently be carried out under suitable conditions. For example, each of the distillations in the esterification of free fatty acids (201) can independently be carried out at elevated temperatures and/or reduced pressures (e.g., under vacuum). Specifically, each of the distillations in the esterification of free fatty acids (201) can independently be carried out at elevated temperatures, e.g., at about 80° C. to about 130° C. Specifically, each of the distillations in the esterification of free fatty acids (201) can independently be carried out at reduced pressures, e.g., about 20 to about 29.92 inches of mercury (Hg).

Each of the distillations in the esterification of free fatty acids (201) can independently be carried out one or more times. Each of the distillations in the esterification of free fatty acids (201) can independently be carried out about 1-5 times, about 1-4 times, about 1-3 times, or about 1-2 times.

In specific embodiments, each of the distillations in the esterification of free fatty acids (201) is independently carried out in a batch mode. Alternatively, in specific embodiments, each of the distillations in the esterification of free fatty acids (201) is independently carried out in a continuous fashion. In specific embodiments, any one or more of the distillations in the esterification of free fatty acids (201) is independently continuous, and includes a single stage distillation column. In alternative specific embodiments, any one or more of the distillations in the esterification of free fatty acids (201) is independently continuous, and includes a multi-stage distillation column. Additionally, each of the single stage (or multi stage) distillation column can independently operate with or without vacuum.

Each of the distillations in the esterification of free fatty acids (201) can independently be carried out on a commercial or industrial scale. For example, any one or more of the distillations in the esterification of free fatty acids (201) can independently be carried out to provide at least about 100 gallons of distillate. Specifically, any one or more of the distillations in the esterification of free fatty acids (201) can independently be carried out to provide, within about 24 hours, at least about 100 gallons of distillate. Additionally, any one or more of the distillations in the esterification of free fatty acids (201) can independently be carried out to provide at least about 1,000 gallons of distillate. Specifically, any one or more of the distillations in the esterification of free fatty acids (201) can independently be carried out to provide, within about 24 hours, at least about 1,000 gallons of distillate.

Reuse of Methanol

The esterification of free fatty acids (201) is carried out with methanol as the reagent. For example, reagent (i.e., methanol) and catalyst are added to the treated biodiesel feedstock (205), to form mixture (207) that includes biodiesel feedstock, methanol, and solid heterogeneous catalyst. As described herein, mixture (207) is subject to esterification (220 or 206) conditions, sufficient to esterify free fatty acids present in the mixture (207). Upon esterification (220 or 206) of free fatty acids present in the mixture (207), reaction product (215 or 209, respectively) is obtained. Because a molar or stoichiometric excess of methanol is typically employed in the esterification (220 or 206), each of reaction products (215 and 209) will typically include methanol. This methanol can be recaptured, purified, and reused for a subsequent esterification (220 or 206), or transesterification (see, FIG. 3).

Specifically, methanol present in reaction product (215) can be separated (212), to provide, e.g., methanol (221), which can be distilled (214) to provide purified methanol (223), which can be reused (218). Likewise, methanol present in reaction product (209) can be separated (208), to provide, e.g., a mixture (211) that includes methanol and water. Mixture (211) can be separated (210), to provide, e.g., methanol (221), which can be distilled (214) to provide purified methanol (223), which can be reused (218).

When a molar or stoichiometric excess of methanol is employed in the esterification (220 or 206), each of reaction products (215 and 209) will typically include methanol. This excess methanol can be recaptured, purified, and reused for a subsequent esterification (220 or 206), or transesterification (see, FIG. 3). In specific embodiments, up to about 100 wt. % of the excess methanol is recaptured, purified, and reused for a subsequent esterification or transesterification. In specific embodiments, at least about 70 wt. % of the excess methanol is recaptured, purified, and reused for a subsequent esterification or transesterification. In more specific embodiments, at least about 80 wt. % of the excess methanol is recaptured, purified, and reused for a subsequent esterification or transesterification. In further specific embodiments, at least about 95 wt. % of the excess methanol is recaptured, purified, and reused for a subsequent esterification or transesterification.

Transesterification of Triglycerides

The transesterification process described herein converts triglycerides (with methanol as reagent, and solid heterogeneous transesterification catalyst) into biodiesel and glycerin. The transesterification process described herein can include a two stage process, with intermediate glycerin settling. The first stage converts about 80 wt. % of the oil (triglycerides), and the second stage converts the remaining approximate 20 wt. % of the oil.

Esterified oil from the esterification process described herein can be mixed with methanol (which is about 15% molar excess than the stoichiometric requirements). Premixed raw materials enter the first stage reactor at a temperature of about 95° F., with a retention time of about 30 minutes. The resultant stream enters a settling tank where biodiesel (along with unreacted oil) is allowed to separate from glycerin (about 4 hours residence time). The biodiesel stream (with unreacted oil) is separated and is allowed to flow from top of the settling tank into the second stage reactor, where it is premixed with methanol (about 15% molar excess).

In the second stage, the remaining oil reacts with methanol at about 95° F. and about 30-45 minutes residence time in the presence of the enzyme catalyst, producing biodiesel and glycerin. The outgoing stream enters a settling tank where the glycerin settles as the bottom layer after about 4 hours of residence time, and the biodiesel stream overflows from the top. Glycerin separated from the two settling tanks are sent to a glycerin purification unit where excess methanol is flashed off and rectified to about 99.8 wt. % purity. Glycerin of a minimum of about 99.7% purity is obtained.

The biodiesel leaving the settling tank passes through a coalescer where trace amounts of glycerin is separated from the biodiesel. Biodiesel leaving the coalescer contains traces of glycerol (less than about 200 ppm), which goes to the final stage of purification with ion resins. The resins adsorb free glycerol and brings the biodiesel to acceptable levels of ASTM D6751 standards. Biodiesel further passes through a distillation column to remove or separate excess methanol and produces biodiesel that has methanol content down to about 2000 μm or less.

Post-transesterification processing can involve a distillation process to effectively remove or separate the contaminants (e.g., sterols, monoglycerides, diglycerides, triglycerides, sulfur, phosphorus, primary and secondary oxidation products, etc.) from the finished biodiesel, thereby producing a superior quality fuel. These contaminants are known to affect the cloud point and cold soak test results on finished biodiesel as per ASTM D6751. Biodiesel resulting from this cold soak has a filtration time of about 200 seconds or less. Biodiesel leaving the cold soak columns can now be analyzed per ASTM D6751 testing standards and once passed is sent to the tank farm for storage.

Glycerin from the settling tanks can first be distilled to remove or separate water and methanol from the glycerin. Relatively clean glycerol can now be sent to a distillation column, where the glycerin is distilled off at relatively high temperatures and under vacuum, to yield a colorless, about 99.7 wt. % pure technical grade glycerin. It can be passed through bed of activated carbon to filter impurities before being sent to the tank farm.

Referring to FIG. 6, a process flow diagram is provided for the transesterification of triglycerides (601), present within a biodiesel feedstock (603). Briefly stated, triglycerides present in the biodiesel feedstock (603) are transesterified (615). Specifically, the biodiesel feedstock (603) is contacted (609) with a transesterifying reagent and catalyst, to provide a transesterification reaction product (617) that includes the desired product biodiesel, the desired product glycerin, and by-product water. When a stoichiometric excess (e.g., 1.25 molar equivalent) of methanol is employed as the transesterifying reagent, the transesterification reaction product (617) will typically include unreacted methanol. The transesterification reaction product (617) is separated (619) to provide biodiesel (623), and a mixture (621) of methanol, water and glycerin.

If the biodiesel contains a significant and appreciable amount of triglycerides (633), the biodiesel (633) is contacted with methanol and transesterification catalyst to form a subsequent transesterification mixture (611), which is subject to transesterification conditions (615), to transesterify triglycerides (633) present therein. The subsequent transesterifying (615) is carried out on the triglycerides present within the subsequent transesterification mixture (611), to provide a subsequent transesterification product (617). The subsequent transesterification product (617) is separated (619), to provide subsequent biodiesel (623), and a subsequent mixture (621) of methanol, water and glycerin. If the subsequent biodiesel (623) contains a significant and appreciable amount of triglycerides (633), the transesterification process is carried out until a subsequent biodiesel (623) does not contain a significant and appreciable amount of triglycerides (633). Once this occurs, the one or more biodiesels (623) will be considered to be a purified biodiesel (639).

The one or more mixtures (621) of methanol, water and glycerin is separated (627), to provide glycerin (633) and a mixture (625) of methanol and water. The glycerin (633) can be purified (635) (e.g., distilled) to provide purified glycerin (643). Additionally, the mixture (625) of methanol and water can be distilled (637) to provide purified methanol (641), which can be reused (613) in a subsequent esterification reaction and/or transesterification reaction.

Figure 3:
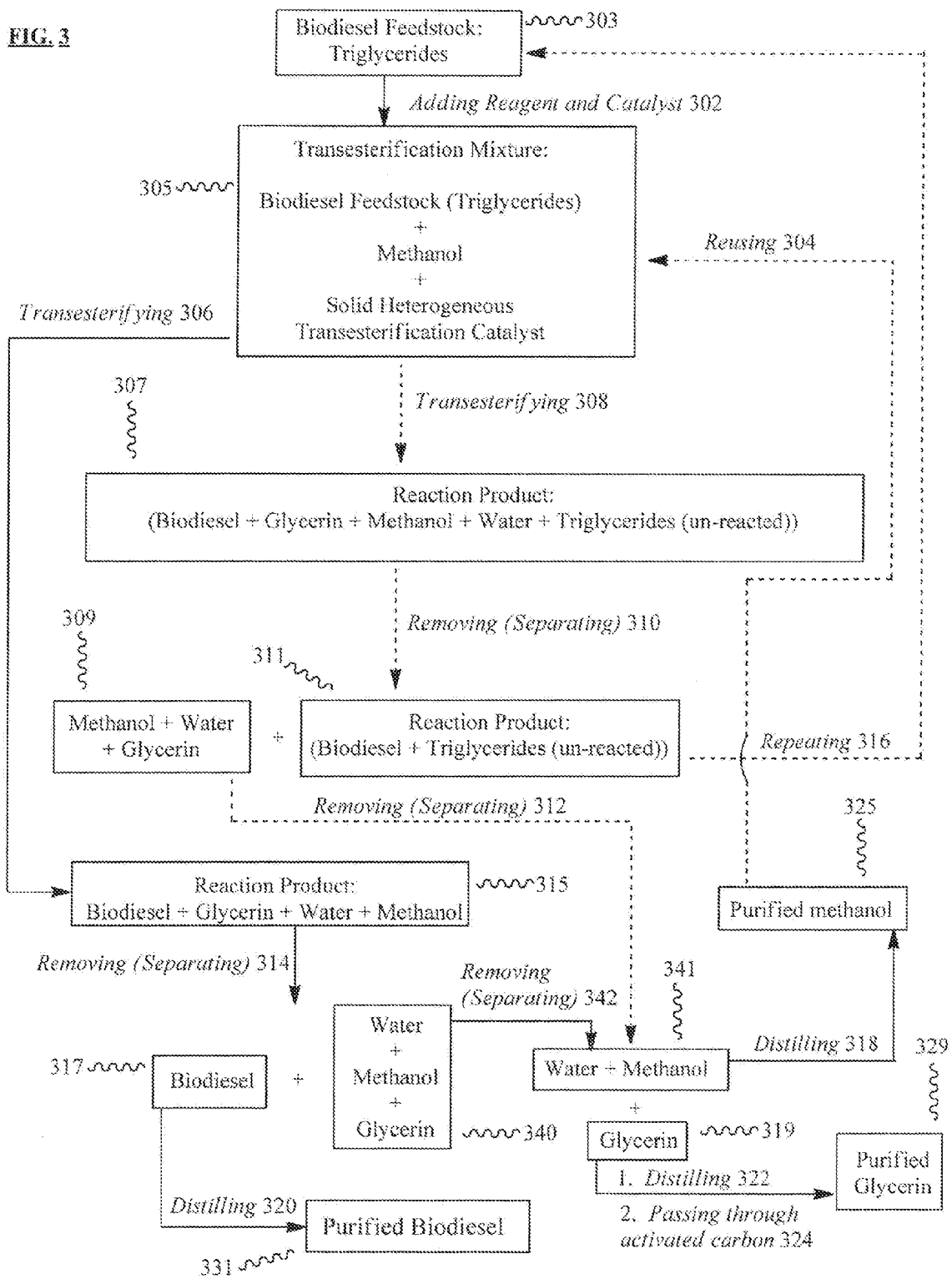
FIG. 3 illustrates a process flow diagram for the transesterification of triglycerides.

Referring to FIG. 3, a process flow diagram is provided for the transesterification of triglycerides (301). Briefly stated, a biodiesel feedstock (303) is contacted (302) with a reagent (e.g., methanol) and catalyst, to provide a mixture (305) that includes a biodiesel feedstock, methanol, and solid heterogeneous catalyst. The biodiesel feedstock (303) can include the biodiesel (217) obtained in the esterification (not shown, see FIG. 2). The mixture (305) that includes a biodiesel feedstock, methanol, and solid heterogeneous catalyst is subject to transesterification conditions (306), to provide a reaction product (315) that includes biodiesel, glycerin, water, and methanol. The reaction product (315) that includes biodiesel, glycerin, water, and methanol is separated (314) into biodiesel (317) and a mixture (340) of glycerin, water, and methanol. The biodiesel (317) is purified, by distilling (320), to provide a purified biodiesel (331). The mixture (340) of glycerin, water, and methanol is separated (342) to provide mixture (341) of water and methanol, which is distilled (318) to provide purified methanol (325). The purified methanol (325) is reused to form a mixture (305).

The mixture (305) that includes a biodiesel feedstock, methanol, and solid heterogeneous catalyst is transesterified (308), to provide a reaction product (307), that includes biodiesel, glycerin, methanol, water, and triglycerides. The reaction product (307) is separated into a mixture (309) of methanol and water, and a reaction product (311) that includes biodiesel and triglycerides. The mixture (309) is separated (312) into a mixture (341) of methanol and water, and glycerin (319). The reaction product (311) can contact (302) reagent and catalyst, to provide the mixture (305), which is subject to transesterification conditions (308), to provide reaction product (307), which is separated (310), to provide reaction product (311) and mixture (309). This process is repeated (316), one or more times, until the final transesterification (306) provides reaction product (315).

Each step of the transesterification of triglycerides (301) can independently be carried out in a continuous fashion, in a batch mode, or in a semi-continuous mode or semi batch mode.

Transesterifying

Mixture (305) that includes biodiesel feedstock, methanol, and solid heterogeneous catalyst is subject to transesterification (306 or 308) conditions. The biodiesel feedstock (303) and the biodiesel feedstock present in mixture (305) can each include triglycerides. These triglycerides present in biodiesel feedstock are transesterified with the methanol, with the aid of the solid heterogeneous catalyst, to provide biodiesel.

Mixture (305) is subject to transesterification (306 or 308) conditions, to provide reaction product (315) that includes biodiesel, water, methanol, and triglycerides. Alternatively, mixture (305) is subject to transesterification (306 or 308) conditions, to provide reaction product (307) that includes biodiesel, glycerin, water, methanol, and triglycerides. When mixture (305) is subject to transesterification (306 or 308) conditions, to provide reaction product (307), mixture (309) that includes methanol, glycerin, and water is separated (310) from the reaction product (307), to provide reaction product (311) that includes biodiesel and triglycerides. Reaction product (311) is subsequently contacted (302) with reagent and catalyst, to form mixture (305), which is subject to transesterification conditions (308). This process (transesterification (308) and separation (310)) is optionally repeated (316) one or more times, until the final transesterifying (306) substantially provides reaction product (315).

The transesterifying (306 or 308) can be carried out under suitable transesterification conditions. Typically, the transesterification (306 or 308) can be carried out at an elevated temperature. In specific embodiments, the methanol, catalyst, and biodiesel feedstock are heated to a temperature of at least about 170° F. (76.67° C.). In further specific embodiments, the methanol, catalyst, and biodiesel feedstock are heated to a temperature of up to about 200° F. (93.33° C.). In further specific embodiments, the methanol, catalyst, and biodiesel feedstock are heated to a temperature of between about 170° F. (76.67° C.) to about 200° F. (93.33° C.).

The transesterifying (306 or 308) can be carried out at an elevated pressure. In specific embodiments, the methanol, catalyst, and biodiesel feedstock are heated at a pressure of at least about 15 psi (1.02 atm). In further specific embodiments, the methanol, catalyst, and biodiesel feedstock are heated at a pressure of up to about 50 psi (3.40 atm).

The transesterifying (306 or 308) is carried out for a requisite period of time. In specific embodiments, the methanol, catalyst, and biodiesel feedstock are heated for a period of time of at least about 15 minutes. In further specific embodiments, the methanol, catalyst, and biodiesel feedstock are heated for a period of time of up to about 75 minutes. In further specific embodiments, the methanol, catalyst, and biodiesel feedstock are heated for a period of time of about 15 minutes to about 75 minutes.

When the transesterifying (306 or 308) is carried out on a commercial or industrial scale, the reagent can be employed in a molar or stoichiometric excess. This will assist in driving the reaction to completion. This is especially so when the transesterifying (308) and separating (310) are carried out one or more times, thereby removing or separating water from each of the one or more reaction products. With the transesterifying (306 or 308) described herein, the methanol can be employed in a molar or stoichiometric excess, relative to the triglycerides content of the biodiesel feedstock.

In specific embodiments, the methanol is employed in at least a 5 molar or stoichiometric excess, relative to the triglycerides content of the biodiesel feedstock. In further specific embodiments, the methanol is employed in at least a 10 molar or stoichiometric excess, relative to the triglycerides content of the biodiesel feedstock. In further specific embodiments, the methanol is employed in at least a 20 molar or stoichiometric excess, relative to the triglycerides content of the biodiesel feedstock. In further specific embodiments, the methanol is employed in up to a 100 molar or stoichiometric excess, relative to the triglycerides content of the biodiesel feedstock.

The transesterifying (306 or 308) provides a reaction product (315 or 307) that aside from water and glycerin, includes relatively few by-products. In specific embodiments, the transesterifying (306 or 308) provides a reaction product (315 or 307) that includes little or no (e.g., less than about 0.5 wt. %) by-product.

The transesterifying (306 or 308) employs methanol as the reagent, present in mixture (305). The methanol will have a requisite purity. For example, in specific embodiments, the methanol will have a purity of at least about 99 wt. %, at least about 99.5 wt. %, at least about 99.9 wt. %, or at least about 99.95 wt. %. In further specific embodiments, the methanol will have a purity of up to about 100 wt. %. Employing methanol having a requisite purity, within the transesterifying (306 or 308), will assist in driving the transesterification (306 or 308) to completion, while providing a relatively high yield and/or purity of desired product.

The transesterifying (306 or 308) employs a solid heterogeneous catalyst, present in the mixture (305). In specific embodiments, the solid heterogeneous catalyst includes Biocatalyst A solid catalyst, Biocatalyst B solid catalyst, or a combination thereof (TransBiodiesel, Israel). In specific embodiments, the solid heterogeneous catalyst is immobilized on a solid support. In specific embodiments, the solid heterogeneous catalyst is non-toxic and is suitable for safely disposal in a land fill. It is believed that by employing a biodiesel (217) as the biodiesel feedstock (303), the commercial life of the solid heterogeneous catalyst will be extended. This can lower the actual cost of the solid heterogeneous catalyst, as well as the labor costs and cost of down-time associated with replacing the solid heterogeneous catalyst.

In specific embodiments, the solid heterogeneous catalyst is active in the transesterification (306 or 308) for at least about 6 months. In further specific embodiments, the solid heterogeneous catalyst is active in the transesterification (306 or 308) for at least about 12 months. In further specific embodiments, the solid heterogeneous catalyst is active in the transesterification (306 or 308) for up to about 18 months.

The transesterifying (308) can be repeated (316) one or more times. As such, the mixture (305) can be subjected to transesterification (308) conditions, to provide reaction product (307), which can be separated into mixture (309) and reaction product (311). Reaction product (311) can subsequently be contacted (302) with reagent and catalyst, to form mixture (305), which can be subjected to transesterification (308) conditions.

The transesterifying (306) is carried out one time. Additionally, the transesterifying (308) is carried out zero or more times. When carried out two or more times, the transesterifying (308) is repeated (316) zero or more times and the transesterifying (306) is carried out one time. In specific embodiments, the transesterifying (308) is carried out about 0-25 times, about 1-15 times, about 1-10 times, or about 1-5 times. In more specific embodiments, the transesterifying (308) is carried out at least about 1 time, at least about 2 times, or at least about 3 times.

In specific embodiments, the repeating (316) is carried out until the final transesterifying (306) substantially provides reaction product (315). In more specific embodiments, the repeating (316) is carried out until the final transesterifying (306) substantially provides reaction product (315), that includes little or no (e.g., less than about 5 wt. %) triglycerides. In further specific embodiments, the repeating (316) is carried out until the final transesterifying (306) provides reaction product (315), that includes less than about 1 wt. % triglycerides. In further specific embodiments, the repeating (316) is carried out until the final transesterifying (306) provides reaction product (315), that includes less than about 0.5 wt. % triglycerides. In further specific embodiments, the repeating (316) is carried out until the final transesterifying (306) provides reaction product (315), that includes less than about 0.1 wt. % triglycerides.

In specific embodiments, the transesterifying (306 or 308) is carried out in a batch mode. Alternatively, in specific embodiments, the transesterifying (306 or 308) is carried out in a continuous fashion.

In specific embodiments, the transesterifying (306 or 308) is continuous, and can include a single stage reactor. In alternative specific embodiments, the transesterifying (306 or 308) is continuous, and can include a multi-stage reactor (e.g., first stage reactor, second stage reactor and third stage reactor). A multi-stage reactor is a reference to transesterifying (306) and one or more transesterifyings (308), in FIG. 3.

When a multi-stage reactor is employed, each stage independently provides for the conversion of triglycerides and methanol to biodiesel, glycerin, and water. In specific embodiments, each stage provides a conversion of at least about 80 wt. % of triglycerides present therein, to biodiesel, glycerin, and water. In more specific embodiments, each stage provides a conversion of at least about 90 wt. % of triglycerides present therein, to biodiesel, glycerin, and water. In further specific embodiments, each stage provides a conversion of at least about 95 wt. % of triglycerides present therein, to biodiesel, glycerin, and water. Additionally, the single stage (or multi stage) reactor can be configured to operate at elevated temperature and/or at elevated pressure.

The transesterifying (306 or 308) can independently be carried out on a commercial or industrial scale. For example, the transesterifying (306 and 308) can be carried out to provide at least about 100 gallons of combined reaction product (307 and 315). Specifically, the transesterifying (306 and 308) can be carried out to provide, within about 24 hours, at least about 100 gallons of combined reaction product (307 and 315). Additionally, the transesterifying (306 and 308) can be carried out to provide at least about 1,000 gallons of combined reaction product (307 and 315). Specifically, the transesterifying (306 and 308) can be carried out to provide, within about 24 hours, at least about 1,000 gallons of combined reaction product (307 and 315).

When the transesterifying (306 or 308) is carried out as described herein, the triglycerides are transesterified with methanol, with a relatively high conversion. In specific embodiments, the triglycerides are transesterified with methanol, with a combined conversion of at least about 70 wt. %. In further specific embodiments, the triglycerides are transesterified with methanol, with a combined conversion of at least about 85 wt. %. In further specific embodiments, the triglycerides are transesterified with methanol, with a combined conversion of at least about 95 wt. %. In further specific embodiments, the triglycerides are transesterified with methanol, with a combined conversion of at least about 98 wt. %. In further specific embodiments, the triglycerides are transesterified with methanol, with a combined conversion of at least about 99 wt. %. In further specific embodiments, the triglycerides are transesterified with methanol, with a combined conversion of up to about 100 wt. %.

Separating/Distilling

Each of the reaction product (307), mixture (309), reaction product (315), and mixture (340) can be separated (310, 314, 312, and (342), respectively). For example, the reaction product (307) can be separated (310) to provide a mixture (309) of methanol and water, and reaction product (311) that includes biodiesel and triglycerides. The mixture (309) can be separated (312) to provide mixture (341) of methanol and water, and glycerin (319). The reaction product (315) can be separated (314) to provide biodiesel (317), and mixture (340) of glycerin, water, and methanol. Mixture (340) can be separated (342) to provide mixture (341) of water and methanol. Each of the separations can independently be carried out, e.g., by employing distillation.

Each of the distillations in the transesterification of triglycerides (301) can independently be carried out under suitable conditions. For example, each of the distillations in the transesterification of triglycerides (301) can independently be carried out at elevated temperatures and/or reduced pressures (e.g., under vacuum). Specifically, each of the distillations in the transesterification of triglycerides (301) can independently be carried out at elevated temperatures, e.g., at about 60° C. to about 530° C. Specifically, each of the distillations in the transesterification of triglycerides (301) can independently be carried out at reduced pressures, e.g., about 24 to about 29.92 inches of mercury (Hg).

Each of the distillations in the transesterification of triglycerides (301) can independently be carried out one or more times. Each of the distillations in the transesterification of triglycerides (301) can independently be carried out about 1-5 times, about 1-4 times, about 1-3 times, or about 1-2 times.

In specific embodiments, each of the distillations in the transesterification of triglycerides (301) is independently carried out in a batch mode. Alternatively, in specific embodiments, each of the distillations in the transesterification of triglycerides (301) is independently carried out in a continuous fashion. In specific embodiments, any one or more of the distillations in the transesterification of triglycerides (301) is independently continuous, and includes a single stage distillation column. In alternative specific embodiments, any one or more of the distillations in the transesterification of triglycerides (301) is independently continuous, and includes a multi-stage distillation column. Additionally, each of the single stage (or multi stage) distillation column can independently operate with or without vacuum.

Each of the distillations in the transesterification of triglycerides (301) can independently be carried out on a commercial or industrial scale. For example, any one or more of the distillations in the transesterification of triglycerides (301) can independently be carried out to provide at least about 100 gallons of distillate. Specifically, any one or more of the distillations in the transesterification of triglycerides (301) can independently be carried out to provide, within about 24 hours, at least about 100 gallons of distillate. Additionally, any one or more of the distillations in the transesterification of triglycerides (301) can independently be carried out to provide at least about 1,000 gallons of distillate. Specifically, any one or more of the distillations in the transesterification of triglycerides (301) can independently be carried out to provide, within about 24 hours, at least about 1,000 gallons of distillate.

Reuse of Methanol

The transesterification of triglycerides (301) is carried out with methanol as the reagent. For example, reagent (i.e., methanol) and catalyst are added to the biodiesel feedstock (303), to form mixture (305) that includes biodiesel feedstock, methanol, and solid heterogeneous catalyst. As described herein, mixture (305) is subject to transesterification (306 or 308) conditions, sufficient to transesterify triglycerides present in the mixture (305). Upon transesterification (306 or 308) of triglycerides present in the mixture (305), reaction product (315 or 307, respectively) is obtained. Because a molar or stoichiometric excess of methanol is typically employed in the transesterification (306 or 308), each of reaction products (315 and 307) will typically include methanol. This methanol can be recaptured, purified, and reused for a subsequent transesterification (306 or 308), or esterification (see, FIG. 2).

Specifically, reaction product (315) can be separated, e.g., into biodiesel (317) and a mixture (340) of water, methanol and glycerin. The mixture (340) can further be separated (342) to mixture (341) of water and methanol. The mixture (341) of water and methanol can be distilled (318) to provide purified methanol (325), which can be reused (304). Likewise, methanol present in reaction product (307) can be separated (310), to provide, e.g., a mixture (309) that includes methanol and water. Mixture (309) can be separated (312), to provide, e.g., mixture (341) of methanol and water, which can be distilled (318) to provide purified methanol (325), which can be reused (304). When a molar or stoichiometric excess of methanol is employed in the transesterification (306 or 308), each of reaction products (315 and 307) will typically include methanol. This excess methanol can be recaptured, purified, and reused for a subsequent transesterification (306 or 308), or esterification (see, FIG. 2). In specific embodiments, up to about 100 wt. % of the excess methanol is recaptured, purified, and reused for a subsequent esterification or transesterification. In specific embodiments, at least about 70 wt. % of the excess methanol is recaptured, purified, and reused for a subsequent esterification or transesterification. In more specific embodiments, at least about 80 wt. % of the excess methanol is recaptured, purified, and reused for a subsequent esterification or transesterification. In further specific embodiments, at least about 95 wt. % of the excess methanol is recaptured, purified, and reused for a subsequent esterification or transesterification.

Enumerated Embodiments

Specific enumerated embodiments [1] to [201] provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

Pretreatment

[1.] The present invention provides for a method that includes:
(a) filtering a biodiesel feedstock, thereby removing or separating solid particles having a diameter up to 2 microns, to provide a filtrate and a retentate;
(b) separating at least one of moisture and water from the filtrate, to provide a dried filtrate;
(c) distilling the dried filtrate, to provide a distillate and a residue;
(d) distilling the distillate to provide a subsequent distillate and optionally a subsequent residue; and;
(e) optionally repeating steps (c) and (d), one or more times, by distilling the subsequent distillate, to obtain a final distillate.

[2.] The present invention also provides for the method of embodiment [1], wherein the biodiesel feedstock further includes at least one of triglycerides, gums, soaps, detergents, unsaponifiables, phosphatides, metals, phosphorus, sulfur, sulfates, sulfonates, sulfides, polyaromatic hydrocarbons, polychlorinated hydrocarbons, polyethylene, plant based sterols, animal based sterols, moisture, and water.

[3.] The present invention also provides for the method of any one of embodiments [1]-[2], wherein the feedstock includes up to about 100 wt. % free fatty acids.

[4.] The present invention also provides for the method of any one of embodiments [1]-[2], wherein the feedstock includes about 0.2 wt. % to about 100 wt. % free fatty acids.

[5.] The present invention also provides for the method of any one of embodiments [1]-[4], wherein the feedstock includes at least one of fats, oils, and grease.

[6.] The present invention also provides for the method of any one of embodiments [1]-[4], wherein the feedstock includes at least one of edible oils, inedible oils, fats, greases, oils produced from microbial/biological/biotechnology/fermentation/metabolic activity, or similar-based process, brown grease, trap grease, used cooking oil, used cooking fat, animal fat, animal grease, and fatty acid distillate.

[7.] The present invention also provides for the method of any one of embodiments [1]-[4], wherein the feedstock includes at least one of tallow, pork fat, poultry fat, lard, choice white grease, algae oil, crude vegetable oils, soybean oil, corn oil, coffee oil, hemp oil, linseed oil, rice bran oil, jojoba oil, tall oil, mustard oil, distillers grain oil (DDG corn oil), *Jatropha* oil, camellia oil, rapeseed oil, canola oil, moring a oil, pongamia oil, sunflower oil, safflower oil, crude palm oil, palm kernel oil, palm fatty acid distillate, palm sludge oil, coconut oil, and their derivatives (including genetically modified and otherwise).

[8.] The present invention also provides for the method of any one of embodiments [1]-[7], wherein at least about 90 wt. % of the solid particles having a diameter of at least about 2 microns are separated, to provide the filtrate and the retentate.

[9.] The present invention also provides for the method of any one of embodiments [1]-[7], wherein up to about 100 wt. % of the solid particles having a diameter of at least about 2 microns are separated, to provide the filtrate and the retentate.

[10.] The present invention also provides for the method of any one of embodiments [1]-[9], wherein the separating of the solid particles is carried out employing multiple filters, each having a smaller porosity or mesh size relative to a previous filter.

[11.] The present invention also provides for the method of any one of embodiments [1]-[10], wherein the biodiesel feedstock includes elevated levels of at least one of water, sulfur, phosphorus, gums/lipids, sterols, calcium, magnesium, iron, copper, cobalt, manganese, nickel, sodium, potassium, chlorophyll, carotenoids, xanthophylls, proteins and carbohydrates, aldehydes, ketones, carboxylic acids, perchloroethylene, polyaromatic hydrocarbons, polychlorinated hydrocarbons, polymerized triglycerides, pesticides, soaps, detergents, sulfonates, sulfates, phosphatides, phytosterols, sitosterols, cholesterol, sterol glucosides, and other colored bodies.

[12.] The present invention also provides for the method of any one of embodiments [1]-[11], wherein the feedstock includes up to about 20,000 ppm of at least one of sulfur, sulfates, sulfides, and sulfonates.

[13.] The present invention also provides for the method of any one of embodiments [1]-[12], wherein the feedstock includes up to about 4000 ppmw phosphorus.

[14.] The present invention also provides for the method of any one of embodiments [1]-[13], which separates from the feedstock at least one of water, sulfur, phosphorus, gums, strerols, calcium, magnesium, iron, copper, sodium, potassium, chlorophyll, phosphatides, and colored bodies.

[15.] The present invention also provides for the method of any one of embodiments [1]-[14], wherein any one or more of the distillings is carried out while heating the feedstock to a temperature of about 100° C. to about 530° C.

[16.] The present invention also provides for the method of any one of embodiments [1]-[14], wherein any one or more of the distillings is carried out while heating the feedstock to a temperature of about 200° C. to about 230° C.

[17.] The present invention also provides for the method of any one of embodiments [1]-[16], wherein any one or more of the distillings is carried out under vacuum, to about 24 to about 29.92 inches of mercury (Hg).

[18.] The present invention also provides for the method of any one of embodiments [1]-[16], wherein any one or more of the distillings is carried out without vacuum.

[19.] The present invention also provides for the method of any one of embodiments [1]-[18], further including recycling the distillate with a reflux ratio of about 0.2 to about 3.5.

[20.] The present invention also provides for the method of any one of embodiments [1]-[19], wherein relative to the distillate, the residue is enriched in at least one of sulfur, phosphorus, gums/lipids, sterols, calcium, magnesium, iron, copper, cobalt, manganese, nickel, sodium, potassium, chlorophyll, carotenoids, xanthophylls, proteins and carbohydrates, aldehydes, ketones, carboxylic acids, perchloroethylene, polyaromatic hydrocarbons, polychlorinated hydrocarbons, polymerized triglycerides, pesticides, soaps, detergents, sulfonates, sulfates, phosphatides, phytosterols, sitosterols, cholesterol, sterol glucosides, oils and fats, other trace impurities, and other colored bodies.

[21.] The present invention also provides for the method of any one of embodiments [1]-[19], wherein relative to the residue, the distillate is enriched in at least one of triglycerides and free fatty acids.

[22.] The present invention also provides for the method of any one of embodiments [1]-[21], wherein the distillate includes up to about 99.995 wt. % triglycerides and free fatty acids.

[23.] The present invention also provides for the method of any one of embodiments [1]-[22], wherein the distillate includes at least one of triglycerides and free fatty acids, wherein the at least one of triglycerides and free fatty acids combined include less than about 7 ppm phosphorus, less than about 7 ppm sulfur, and less than about 10 ppm of all other metals combined.

[24.] The present invention also provides for the method of any one of embodiments [1]-[23], wherein the distillate includes at least one of triglycerides and free fatty acids, wherein the at least one of triglycerides and free fatty acids combined include less than about 7 ppm sulfur.

[25.] The present invention also provides for the method of any one of embodiments [1]-[24], wherein a weight of the retentate is up to about 0.2% a weight of the feedstock.

[26.] The present invention also provides for the method of any one of embodiments [1]-[25], wherein the retentate is non-toxic and suitable for safe disposal in a land fill.

[27.] The present invention also provides for the method of any one of embodiments [1]-[26], wherein the weight of the residue is about 0.2% to about 6% the weight of the dried filtrate.

[28.] The present invention also provides for the method of any one of embodiments [1]-[27], wherein distilling the one or more subsequent distillates includes a single stage distillation column, operating with or without vacuum.

[29.] The present invention also provides for the method of any one of embodiments [1]-[28], wherein the continuously distilling includes a multi-stage distillation column.

[30.] The present invention also provides for the method of any one of embodiments [1]-[29], wherein at least about 100 gallons of biodiesel feedstock is employed.

[31.] The present invention also provides for the method of any one of embodiments [1]-[29], wherein up to about 1,000 gallons of biodiesel feedstock is employed.

[32.] The present invention also provides for the method of any one of embodiments [1]-[31], wherein at least about 100 gallons of the distillate is obtained, within 24 hours.

[33.] The present invention also provides for the method of any one of embodiments [1]-[31], wherein up to about 1,000 gallons of the distillate is obtained, within 24 hours.

[34.] The present invention also provides for the method of any one of embodiments [1]-[33], wherein prior to the process, the biodiesel feedstock is analyzed to determine a qualitative nature of impurities located therein.

[35.] The present invention also provides for the method of any one of embodiments [1]-[33], wherein prior to the process, the biodiesel feedstock is analyzed to determine a quantitative nature of impurities located therein.

[36.] The present invention also provides for the method of any one of embodiments [1]-[35], wherein the filtering is carried out in the presence of an adsorbent.

[37.] The present invention also provides for the method of any one of embodiments [1]-[35], wherein the filtering is carried out in the absence of an adsorbent.

[38.] The present invention also provides for the method of any one of embodiments [1]-[37], which is a method for separating from biodiesel feedstock at least one of water, sulfur, phosphorus, gums/lipids, sterols, calcium, magnesium, iron, copper, cobalt, manganese, nickel, sodium, potassium, chlorophyll, carotenoids, xanthophylls, proteins and carbohydrates, aldehydes, ketones, carboxylic acids, perchloroethylene, polyaromatic hydrocarbons, polychlorinated hydrocarbons, polymerized triglycerides, pesticides, soaps, detergents, sulfonates, sulfates, phosphatides, phytosterols, sitosterols, cholesterol, sterol glucosides, oils and fats, other trace impurities, and other colored bodies.

[39.] The present invention also provides for the method of any one of embodiments [1]-[38], which does not include adding water.

[40.] The present invention also provides for the method of any one of embodiments [1]-[39], wherein the distillate and the residue are separated.

[41.] The present invention also provides for the method of any one of embodiments [1]-[40], which is a method of purifying a biodiesel feedstock.

[42.] The present invention also provides for the method of any one of embodiments [1]-[41], wherein the distillate and the residue are separated, and the distillate is subsequently distilled to provide the subsequent distillate and the subsequent residue.

[43.] The present invention also provides for the method of any one of embodiments [1]-[41], wherein the distillate and the residue are separated, the distillate is subsequently distilled to provide the subsequent distillate and the subsequent residue, and the method is repeated one or more times.

[44.] The present invention also provides for the method of any one of embodiments [1]-[41], wherein the distillate and the residue are separated, the distillate is subsequently distilled to provide the subsequent distillate and the subsequent residue, and the method is repeated one or more times, until no appreciable or significant amount of residue is obtained.

[45.] The present invention also provides for the method of any one of embodiments [1]-[44], wherein the distillate and the residue are separated, and the distillate is stored as a purified biodiesel feedstock.

[46.] The present invention also provides for the method of any one of embodiments [1]-[45], wherein the steps (c) and (d) are repeated, one or more times, by distilling the subsequent distillate, to obtain a final distillate.

[47.] The present invention also provides for the method of any one of embodiments [1]-[46], wherein the steps (c) and (d) are repeated, two or more times, by distilling the subsequent distillate, to obtain a final distillate.

[48.] The present invention also provides for the method of any one of embodiments [1]-[47], wherein the feedstock includes one or more of the feedstock impurities illustrated in Table A.

[49.] The present invention also provides for the method of any one of embodiments [1]-[47], wherein the feedstock includes each of the feedstock impurities illustrated in Table A.

[50.] The present invention also provides for the method of any one of embodiments [1]-[47], wherein the feedstock includes one or more of the feedstock impurities illustrated in Table A, each in the amount disclosed therein.

[51.] The present invention also provides for the method of any one of embodiments [1]-[47], wherein the feedstock includes each of the feedstock impurities illustrated in Table A, each in the amount disclosed therein.

Esterification

[52.] The present invention provides for a method including:

(a) contacting (i) methanol, (ii) a solid heterogeneous esterification catalyst, and (iii) a biodiesel feedstock including free fatty acids, wherein the contacting is carried out under conditions suitable to provide an esterification reaction product including biodiesel, methanol, water, and optionally free fatty acids;

(b) separating water and methanol from the esterification reaction product;

(c) contacting the esterification reaction product with (i) methanol and (iii) a solid heterogeneous esterification catalyst, wherein the contacting is carried out under conditions suitable to provide a subsequent esterification reaction product including biodiesel, methanol, water and optionally free fatty acids; and (d) optionally repeating steps (b) and (c) one or more times, to provide an esterification reaction product including biodiesel;

wherein the methanol separated from the one or more esterification reaction products is purified to a purity of at least about 99.9 wt. %, and is employed in a subsequent esterification.

[53.] The present invention also provides for the method of embodiment [52], which is a method for esterifying, with methanol, free fatty acids present in a biodiesel feedstock.

[54.] The present invention also provides for the method of any one of embodiments [52]-[53], wherein the biodiesel feedstock including free fatty acids includes a distillate obtained from a pretreatment process.

[55.] The present invention also provides for the method of any one of embodiments [52]-[54], which is carried out in the absence of a toxic mineral acid.

[56.] The present invention also provides for the method of any one of embodiments [52]-[55], which is carried out in the absence of phosphoric acid, sulfuric acid, hydrochloric acid, citric acid, or a combination thereof.

[57.] The present invention also provides for the method of any one of embodiments [52]-[56], wherein the free fatty acids are esterified with methanol, with a conversion of at least about 70 wt. %.

[58.] The present invention also provides for the method of any one of embodiments [52]-[56], wherein the free fatty acids are esterified with methanol, with a conversion of up to about 100 wt. %.

[59.] The present invention also provides for the method of any one of embodiments [52]-[58], wherein the free fatty acids are esterified with methanol, with no soap product, no salt product, or any by-product.

[60.] The present invention also provides for the method of any one of embodiments [52]-[59], wherein the solid heterogeneous catalyst lasts at least about 6 months.

[61.] The present invention also provides for the method of any one of embodiments [52]-[59], wherein the solid heterogeneous catalyst lasts up to about 18 months.

[62.] The present invention also provides for the method of any one of embodiments [52]-[61], wherein the biodiesel feedstock, prior to contacting the methanol, is pretreated to separate trace elements, impurities and foulants selected from gums, metals, cations, proteins, and phospholipids.

[63.] The present invention also provides for the method of any one of embodiments [52]-[62], wherein the biodiesel feedstock is premixed with methanol, and prior to contacting the methanol, is pretreated at standard temperature.

[64.] The present invention also provides for the method of any one of embodiments [52]-[62], wherein the biodiesel feedstock is not premixed with methanol, and prior to contacting the methanol, is pretreated at standard temperature.

[65.] The present invention also provides for the method of any one of embodiments [52]-[62], wherein the biodiesel feedstock is premixed with methanol, and prior to contacting the methanol, is pretreated at standard pressure.

[66.] The present invention also provides for the method of any one of embodiments [52]-[62], wherein the biodiesel feedstock is not premixed with methanol, and prior to contacting the methanol, is pretreated at standard pressure.

[67.] The present invention also provides for the method of any one of embodiments [52]-[66], wherein the biodiesel feedstock, prior to contacting the methanol, is pretreated by passing through an ion exchange resin.

[68.] The present invention also provides for the method of any one of embodiments [52]-[66], wherein the biodiesel feedstock, prior to contacting the methanol, is pretreated with an ion exchange resin, which consists of a straight, flow-through 2 stage guard bed column reactors in series.

[69.] The present invention also provides for the method of any one of embodiments [52]-[68], wherein the solid heterogeneous catalyst includes a solid, heterogeneous, polymeric esterification catalyst.

[70.] The present invention also provides for the method of any one of embodiments [52]-[69], wherein the methanol, catalyst, and biodiesel feedstock are heated to a temperature of at least about 170° F. (76.67° C.).

[71.] The present invention also provides for the method of any one of embodiments [52]-[69], wherein the methanol, catalyst, and biodiesel feedstock are heated to a temperature of up to about 200° F. (93.33° C.).

[72.] The present invention also provides for the method of any one of embodiments [52]-[71], wherein the methanol, catalyst, and biodiesel feedstock are heated at a pressure of at least about 15 psi (1.02 atm).

[73.] The present invention also provides for the method of any one of embodiments [52]-[71], wherein the methanol, catalyst, and biodiesel feedstock are heated at a pressure of up to about 50 psi (3.40 atm).

[74.] The present invention also provides for the method of any one of embodiments [52]-[73], wherein the methanol, catalyst, and biodiesel feedstock are heated for a period of time of at least about 15 minutes.

[75.] The present invention also provides for the method of any one of embodiments [52]-[73], wherein the methanol, catalyst, and biodiesel feedstock are heated for a period of time of up to about 75 minutes.

[76.] The present invention also provides for the method of any one of embodiments [52]-[75], wherein the methanol is employed in a stoichiometric excess, relative to the free fatty acid content of the biodiesel feedstock.

[77.] The present invention also provides for the method of any one of embodiments [52]-[75], wherein the methanol is employed in up to about a 100% molar excess, relative to the free fatty acid content of the biodiesel feedstock.

[78.] The present invention also provides for the method of any one of embodiments [52]-[77], further including separating the water from the biodiesel.

[79.] The present invention also provides for the method of any one of embodiments [52]-[77], further including separating the water from the biodiesel by employing a flash column, with demister pads and under vacuum.

[80.] The present invention also provides for the method of any one of embodiments [52]-[79], further including separating un-reacted methanol from the biodiesel.

[81.] The present invention also provides for the method of any one of embodiments [52]-[79], further including separating un-reacted methanol from the biodiesel, by employing a flash column, with demister pads and under vacuum.

[82.] The present invention also provides for the method of any one of embodiments [52]-[79], further including separating un-reacted methanol from the biodiesel, purifying the separated methanol to a purity of at least about 99.9%, and employing the purified methanol in a subsequent biodiesel esterification or biodiesel transesterification.

[83.] The present invention also provides for the method of any one of embodiments [52]-[82], which is carried out including a first stage reactor, a second stage reactor and a third stage reactor.

[84.] The present invention also provides for the method of any one of embodiments [52]-[82], which is carried out including a first stage reactor, a second stage reactor and a third stage reactor, wherein each stage independently provides for the conversion of free fatty acids and methanol to biodiesel and water.

[85.] The present invention also provides for the method of any one of embodiments [52]-[82], which is carried out including a first stage reactor, a second stage reactor and a third stage reactor, wherein each stage independently provides for the conversion of free fatty acids and methanol to biodiesel and water, with a conversion at each stage of at least about 90 wt. %.

[86.] The present invention also provides for the method of any one of embodiments [52]-[82], which is carried out including a first stage reactor, wherein upon conversion of free fatty acid present in the biodiesel feedstock to biodiesel, water and excess methanol are separated from the reaction product.

[87.] The present invention also provides for the method of any one of embodiments [52]-[82], which is carried out including a first stage reactor, wherein upon conversion of free fatty acid present in the biodiesel feedstock to biodiesel, water and methanol are separated from the reaction product, and the methanol is subsequently purified.

[88.] The present invention also provides for the method of any one of embodiments [52]-[82], which is carried out including a first stage reactor, wherein upon conversion of free fatty acid present in the biodiesel feedstock to biodiesel, water and methanol are separated from the biodiesel, triglycerides, and un-reacted free fatty acids, and transferred to a second stage reactor.

[89.] The present invention also provides for the method of any one of embodiments [52]-[88], further including transferring biodiesel, triglycerides, and un-reacted free fatty acids from a first stage reactor to a send stage reactor, wherein the biodiesel, triglycerides, and un-reacted free fatty acids include less than about 1 wt. % water.

[90.] The present invention also provides for the method of any one of embodiments [52]-[89], further including transferring biodiesel, triglycerides, and un-reacted free fatty acids from a first stage reactor to a second stage reactor, wherein the biodiesel, triglycerides, and un-reacted free fatty acids include less than about 1 wt. % methanol.

[91.] The present invention also provides for the method of any one of embodiments [52]-[90], further including transferring biodiesel, triglycerides, and un-reacted free fatty acids from a first stage reactor to a second stage reactor, and contacting with methanol having a purity of at least about 98 wt. % pure.

[92.] The present invention also provides for the method of any one of embodiments [52]-[91], further including transferring biodiesel, triglycerides, and un-reacted free fatty acids from a first stage reactor to a second stage reactor, and contacting with a stoichiometric excess of methanol, relative to the free fatty acid content of the biodiesel.

[93.] The present invention also provides for the method of any one of embodiments [52]-[91], further including transferring biodiesel, triglycerides, and un-reacted free fatty acids from a first stage reactor to a second stage reactor, and contacting with up to about a 100% molar excess of methanol, relative to the free fatty acid content of the biodiesel.

[94.] The present invention also provides for the method of any one of embodiments [52]-[93], wherein the biodiesel includes less than about 1 wt. % free fatty acid.

[95.] The present invention also provides for the method of any one of embodiments [52]-[94], wherein the biodiesel further includes triglycerides.

[96.] The present invention also provides for the method of any one of embodiments [52]-[95], wherein the water is separated from the biodiesel, such that the biodiesel includes less than about 1.5 wt. % water.

[97.] The present invention also provides for the method of any one of embodiments [52]-[96], wherein un-reacted methanol is separated from the biodiesel, such that the biodiesel includes less than about 1.5 wt. % methanol.

[98.] The present invention also provides for the method of any one of embodiments [52]-[97], which provides for a crude reaction product including water, methanol, biodiesel, triglycerides and free fatty acid.

[99.] The present invention also provides for the method of any one of embodiments [52]-[98], which provides for a crude reaction product including water, methanol, biodiesel, triglycerides and free fatty acid; and the method further including separating at least one of water and methanol from the crude reaction product.

[100.] The present invention also provides for the method of any one of embodiments [52]-[99], which provides for a crude reaction product including water, methanol, biodiesel, triglycerides and free fatty acid; and the method further including separating at least one of water and methanol from the crude reaction product under vacuum of 29.92 inches of mercury (Hg), or less.

[101.] The present invention also provides for the method of any one of embodiments [52]-[100], which provides for a crude reaction product including water, methanol, biodiesel, triglycerides and free fatty acid; and the method further including separating at least one of water and methanol from the crude reaction product at a temperature of at least about 170° F. (76.67° C.).

[102.] The present invention also provides for the method of any one of embodiments [52]-[101], which provides for a crude reaction product including water, methanol, biodiesel, triglycerides and free fatty acid, and wherein the biodiesel and triglycerides are not subsequently separated from one another.

[103.] The present invention also provides for the method of any one of embodiments [52]-[102], wherein at least about 100 gallons of biodiesel feedstock is employed.

[104.] The present invention also provides for the method of any one of embodiments [52]-[102], wherein up to about 1,000 gallons of biodiesel feedstock is employed.

[105.] The present invention also provides for the method of any one of embodiments [52]-[104], wherein at least about 100 gallons of biodiesel is obtained, within 24 hours.

[106.] The present invention also provides for the method of any one of embodiments [52]-[104], wherein up to about 1,000 gallons of biodiesel is obtained, within 24 hours.

[107.] The present invention also provides for the method of any one of embodiments [52]-[106], wherein the catalyst is non-toxic and suitable for safely disposal in a land fill.

[108.] The present invention also provides for the method of any one of embodiments [52]-[107], wherein the catalyst is immobilized on a solid support.

[109.] The present invention also provides for the method of any one of embodiments [52]-[108], wherein the methanol is obtained from a previous esterification.

[110.] The present invention also provides for the method of any one of embodiments [52]-[109], carried out in a continuous fashion.

[111.] The present invention also provides for the method of any one of embodiments [52]-[110], carried out in a batch mode.

[112.] The present invention also provides for the method of any one of embodiments [52]-[111], wherein the free fatty acids present in the biodiesel feedstock are esterified with methanol to provide a reaction product including biodiesel, water, triglycerides, and un-reacted methanol.

[113.] The present invention also provides for the method of any one of embodiments [52]-[111], wherein the free fatty acids present in the biodiesel feedstock are esterified with methanol to provide a reaction product including biodiesel, water, triglycerides, un-reacted methanol, and un-reacted free fatty acids.

[114.] The present invention also provides for the method of any one of embodiments [52]-[111], wherein the free fatty acids present in the biodiesel feedstock are esterified with methanol to provide a reaction product including biodiesel, water, triglycerides, un-reacted methanol, and un-reacted free fatty acids; and at least one of water and methanol are separated from the reaction product.

[115.] The present invention also provides for the method of any one of embodiments [52]-[111], wherein the free fatty acids present in the biodiesel feedstock are esterified with methanol to provide a reaction product including biodiesel, water, triglycerides, un-reacted methanol, and un-reacted free fatty acids;

at least one of water and methanol are separated from the reaction product; and the reaction product including biodiesel, triglycerides, and free fatty acids is subsequently esterified to provide a subsequent reaction product including biodiesel, water, triglycerides, un-reacted methanol, and optionally free fatty acids.

[116.] The present invention also provides for the method of any one of embodiments [52]-[111], wherein the free fatty acids present in the biodiesel feedstock are esterified with methanol to provide a reaction product including biodiesel, water, triglycerides, un-reacted methanol, and un-reacted free fatty acids;

at least one of water and methanol are separated from the reaction product;

the reaction product including biodiesel, triglycerides, and free fatty acids is subsequently esterified to provide a subsequent reaction product including biodiesel, water, triglycerides, un-reacted methanol, and optionally free fatty acids; and the separation and esterification are optionally repeated one or more times until a further subsequent reaction product does not include a significant or appreciable amount of free fatty acids.

[117.] The present invention also provides for the method of any one of embodiments [114]-[116], wherein both water and methanol are separated from the one or more esterification reaction products.

[118.] The present invention also provides for the method of any one of embodiments [52]-[117], wherein the biodiesel feedstock including free fatty acids includes the final distillate of any one of embodiments [1]-[51].

Transesterification

[119.] The present invention provides for a method including:

(a) contacting at a temperature of less than 102° F. (38.89° C.) (i) methanol, (ii) a solid heterogeneous transesterification catalyst, and (iii) a biodiesel feedstock including triglycerides, wherein the contacting is carried out under conditions suitable to provide a biodiesel, methanol, water, glycerin and optionally triglycerides;

(b) separating water, glycerin and methanol from the transesterification reaction product;

(c) contacting the transesterification reaction product with (i) methanol and (ii) a solid heterogeneous transesterification catalyst, wherein the contacting is carried out under conditions suitable to provide a subsequent transesterification reaction product including biodiesel, methanol, water, glycerin and optionally triglycerides; and (d) optionally repeating steps (b) and (c) one or more times, to provide a transesterification reaction product including biodiesel and glycerin;

wherein the methanol separated from the one or more transesterification reaction products is purified to a purity of at least about 99.9 wt. %, and is employed in a subsequent transesterification.

[120.] The present invention also provides for the method of embodiment [119], which is a method for transesterifying, with methanol, triglycerides present in a biodiesel feedstock.

[121.] The present invention also provides for the method of any one of embodiments [119]-[120], wherein the catalyst is a transesterification enzyme catalyst.

[122.] The present invention also provides for the method of any one of embodiments [119]-[121], wherein the biodiesel feedstock including triglycerides includes an esterification reaction product including biodiesel.

[123.] The present invention also provides for the method of any one of embodiments [119]-[122], wherein the catalyst is non-toxic and suitable for safe disposal in a land fill.

[124.] The present invention also provides for the method of any one of embodiments [119]-[123], wherein the catalyst is an enzyme biocatalyst.

[125.] The present invention also provides for the method of any one of embodiments [119]-[124], wherein the catalyst is immobilized on a solid support.

[126.] The present invention also provides for the method of any one of embodiments [119]-[125], wherein the catalyst has a stability such that less than about 5 wt. % will degrade at standard temperature and pressure within 1 year.

[127.] The present invention also provides for the method of any one of embodiments [119]-[126], wherein the contacting is carried out at a temperature of 95° F. (35° C.), ±6° F.

[128.] The present invention also provides for the method of any one of embodiments [119]-[127], carried out in the absence of sodium methylate.

[129.] The present invention also provides for the method of any one of embodiments [119]-[128], wherein the reaction mixture including methanol, biodiesel feedstock and heterogeneous solid catalyst optionally further includes up to about 1 wt. % water.

[130.] The present invention also provides for the method of any one of embodiments [119]-[129], which includes a first stage reactor and a second stage reactor.

[131.] The present invention also provides for the method of any one of embodiments [119]-[130], wherein the methanol is employed in a stoichiometric excess, relative to the triglycerides content of the biodiesel feedstock.

[132.] The present invention also provides for the method of any one of embodiments [119]-[130], wherein the methanol is employed in up to about a 20% molar excess, relative to the triglycerides content of the biodiesel feedstock.

[133.] The present invention also provides for the method of any one of embodiments [119]-[132], wherein the methanol, catalyst, and biodiesel feedstock are heated for a period of time of at least about 15 minutes.

[134.] The present invention also provides for the method of any one of embodiments [119]-[132], wherein the methanol, catalyst, and biodiesel feedstock are heated for a period of time of up to about 75 minutes.

[135.] The present invention also provides for the method of any one of embodiments [119]-[134], which provides for a crude reaction product including biodiesel, triglycerides, glycerin, methanol, and water;

the method further including separating at least one of methanol and water from the crude reaction product.

[136.] The present invention also provides for the method of any one of embodiments [119]-[134], which provides for a crude reaction product including biodiesel, triglycerides, glycerin, methanol, and water;

the method further including separating at least one of methanol and water from the crude reaction product and purifying the methanol.

[137.] The present invention also provides for the method of any one of embodiments [119]-[134], which provides for a crude reaction product including biodiesel, triglycerides, glycerin, methanol, and water;

the method further including separating at least one of methanol and water from the crude reaction product, purifying the methanol, and reusing the purified methanol in a subsequent transesterification.

[138.] The present invention also provides for the method of any one of embodiments [119]-[136], which provides for a crude reaction product including biodiesel, triglycerides, glycerin, methanol, and water;

the method further including separating triglycerides from the crude reaction product.

[139.] The present invention also provides for the method of any one of embodiments [119]-[136], which provides for a crude reaction product including biodiesel, triglycerides, glycerin, methanol, and water;

the method further including separating triglycerides from the crude reaction product and transferring the triglycerides to a second stage reactor and contacting the triglycerides with methanol having a purity of at least about 98 wt. % pure.

[140.] The present invention also provides for the method of any one of embodiments [119]-[136], which provides for a crude reaction product including biodiesel, triglycerides, glycerin, methanol, and water;

the method further including separating biodiesel and triglycerides from the crude reaction product and transferring the biodiesel and triglycerides to a second stage reactor and contacting the biodiesel and triglycerides with methanol having a purity of at least about 98 wt. % pure.

[141.] The present invention also provides for the method of any one of embodiments [119]-[140], wherein the methanol is obtained from a previous transesterification.

[142.] The present invention also provides for the method of any one of embodiments [119]-[141], which provides for a crude reaction product including biodiesel, triglycerides, glycerin, methanol, and water;

the method further including separating glycerin from the crude reaction product.

[143.] The present invention also provides for the method of any one of embodiments [119]-[142], further including purifying the biodiesel.

[144.] The present invention also provides for the method of any one of embodiments [119]-[142], further including purifying the biodiesel from at least one of water, methanol, glycerol, sterols, monoglycerides, diglycerides, and triglycerides.

[145.] The present invention also provides for the method of any one of embodiments [119]-[144], wherein at least about 90 wt. % of the triglycerides present in the biodiesel feedstock are converted to the biodiesel.

[146.] The present invention also provides for the method of any one of embodiments [119]-[144], wherein up to about 100 wt. % of the triglycerides present in the biodiesel feedstock are converted to the biodiesel.

[147.] The present invention also provides for the method of any one of embodiments [119]-[146], wherein the biodiesel is at least about 99 wt. % pure.

[148.] The present invention also provides for the method of any one of embodiments [119]-[147], wherein the biodiesel includes less than about 2,000 ppmw of methanol.

[149.] The present invention also provides for the method of any one of embodiments [119]-[148], wherein the biodiesel includes less than about 0.24 wt. % of total glycerol.

[150.] The present invention also provides for the method of any one of embodiments [119]-[148], wherein the biodiesel includes less than about 0.18 wt. % of total glycerol.

[151.] The present invention also provides for the method of any one of embodiments [119]-[148], wherein the biodiesel includes no more than about 0.12 wt. % of total glycerol.

[152.] The present invention also provides for the method of any one of embodiments [119]-[148], wherein the biodiesel includes less than about 0.05 wt. % of free glycerin.

[153.] The present invention also provides for the method of any one of embodiments [119]-[148], wherein the biodiesel includes less than about 300 ppmw of free glycerin.

[154.] The present invention also provides for the method of any one of embodiments [119]-[148], wherein the biodiesel includes no more than about 200 ppmw of free glycerin.

[155.] The present invention also provides for the method of any one of embodiments [119]-[154], wherein the biodiesel includes less than about 0.5 acid number.

[156.] The present invention also provides for the method of any one of embodiments [119]-[154], wherein the biodiesel includes less than about 0.4 acid number.

[157.] The present invention also provides for the method of any one of embodiments [119]-[154], wherein the biodiesel includes no more than about 0.2 acid number.

[158.] The present invention also provides for the method of any one of embodiments [119]-[157], wherein the biodiesel has a flash point of at least about 120° C.

[159.] The present invention also provides for the method of any one of embodiments [119]-[157], wherein the biodiesel has a flash point of at least about 150° C.

[160.] The present invention also provides for the method of any one of embodiments [119]-[157], wherein the biodiesel has a flash point of at least about 170° C.

[161.] The present invention also provides for the method of any one of embodiments [119]-[160], wherein the biodiesel has a moisture content of less than about 200 ppmw.

[162.] The present invention also provides for the method of any one of embodiments [119]-[160], wherein the biodiesel has a moisture content of no more than about 50 ppmw.

[163.] The present invention also provides for the method of any one of embodiments [119]-[162], wherein the biodiesel has a sulfur content that is less than about 15 ppm.

[164.] The present invention also provides for the method of any one of embodiments [119]-[162], wherein the biodiesel has a sulfur content that is less than about 10 ppm.

[165.] The present invention also provides for the method of any one of embodiments [119]-[162], wherein the biodiesel has a sulfur content that is less than about 5 ppm.

[166.] The present invention also provides for the method of any one of embodiments [119]-[165], wherein the biodiesel has a phosphorus content that is less than about 15 ppm.

[167.] The present invention also provides for the method of any one of embodiments [119]-[165], wherein the biodiesel has a phosphorus content that is less than about 10 ppm.

[168.] The present invention also provides for the method of any one of embodiments [119]-[165], wherein the biodiesel has a phosphorus content that is less than about 5 ppm.

[169.] The present invention also provides for the method of any one of embodiments [119]-[168], wherein the biodiesel has a content of polymerized triglycerides that is less than about 15 ppm.

[170.] The present invention also provides for the method of any one of embodiments [119]-[169], wherein the biodiesel has a content of polymerized triglycerides that is less than about 10 ppm.

[171.] The present invention also provides for the method of any one of embodiments [119]-[170], wherein the biodiesel has a content of polymerized triglycerides that is less than about 5 ppm.

[172.] The present invention also provides for the method of any one of embodiments [119]-[171], wherein the biodiesel has a sterols content that is less than about 25 ppm.

[173.] The present invention also provides for the method of any one of embodiments [119]-[171], wherein the biodiesel has a sterols content that is less than about 15 ppm.

[174.] The present invention also provides for the method of any one of embodiments [119]-[171], wherein the biodiesel has a sterols content that is less than about 10 ppm.

[175.] The present invention also provides for the method of any one of embodiments [119]-[174], carried out in a continuous fashion.

[176.] The present invention also provides for the method of any one of embodiments [119]-[174], carried out in a batch mode.

[177.] The present invention also provides for the method of any one of embodiments [119]-[176], wherein any triglycerides, diglycerides, and monoglycerides present in the biodiesel feedstock are transesterified with methanol, to provide a reaction product including biodiesel, glycerin, water, and un-reacted methanol.

[178.] The present invention also provides for the method of any one of embodiments [119]-[176], wherein any triglycerides, diglycerides, and monoglycerides present in the biodiesel feedstock are transesterified with methanol, to provide a reaction product including biodiesel, glycerin, water, un-reacted methanol, and optionally un-reacted triglycerides.

[179.] The present invention also provides for the method of any one of embodiments [119]-[176], wherein any triglycerides, diglycerides, and monoglycerides present in the biodiesel feedstock are transesterified with methanol, to provide a reaction product including biodiesel, glycerin, water, un-reacted methanol, and optionally un-reacted triglycerides; and at least one of methanol, water, and glycerin are separated from the reaction product.

[180.] The present invention also provides for the method of any one of embodiments [119]-[176], wherein the triglycerides present in the biodiesel feedstock are transesterified with methanol, to provide a reaction product including biodiesel, glycerin, water, un-reacted methanol, and optionally un-reacted triglycerides, diglycerides, and monoglycerides;
at least one of methanol, water, and glycerin are separated from the reaction product; and
the reaction product including biodiesel and un-reacted triglycerides, diglycerides, and monoglycerides are subsequently transesterified to provide a subsequent reaction product including biodiesel, glycerin, water, and un-reacted methanol.

[181.] The present invention also provides for the method of any one of embodiments [119]-[176], wherein the triglycerides present in the biodiesel feedstock are transesterified with methanol, to provide a reaction product including biodiesel, glycerin, water, un-reacted methanol, and optionally un-reacted triglycerides, diglycerides, and monoglycerides;
at least one of methanol, water, and glycerin are separated from the reaction product;
the reaction product including biodiesel and un-reacted triglycerides, diglycerides, and monoglycerides are subsequently transesterified to provide a subsequent reaction product including biodiesel, glycerin, water, and un-reacted methanol; and
the separation and transesterification are optionally repeated one or more times.

[182.] The present invention also provides for the method of embodiment [181], the separation and transesterification are optionally repeated one or more times until a further subsequent reaction product does not include an appreciable or significant amount of un-reacted triglycerides, diglycerides, and monoglycerides.

[183.] The present invention also provides for the method of any one of embodiments [179]-[181], wherein each of methanol, water, and glycerin are separated from the one or more reaction products.

[184.] The present invention also provides for the method of any one of embodiments [179]-[181], wherein each of methanol, water, and glycerin are separated from the reaction product and the one or more subsequent reaction products;
the glycerin is separated from the water and methanol;
the glycerin is distilled; and
the glycerin is passed through activated carbon.

[185.] The present invention also provides for the method of embodiment [184], wherein the glycerin is distilled in a distillation column, optionally under vacuum.

[186.] The present invention also provides for the method of embodiment [185], wherein the glycerin is distilled in a distillation column, at a temperature of about 100-350° C.

[187.] The present invention also provides for the method of embodiment [185], wherein the glycerin is passed through activated carbon to eliminate impurities.

[188.] The present invention also provides for the method of embodiment [185], wherein the glycerin obtained therein has a technical grade of at least 95 wt. % purity.

[189.] The present invention also provides for the method of any one of embodiments [179]-[181], wherein the biodiesel is separated from the reaction product and the one or more subsequent reaction products.

[190.] The present invention also provides for the method of embodiment [189], wherein reaction product and the one or more subsequent reaction products include at least one of sterols, sulfur, sulfates, sulfones, sulfides, phosphorus, monoglycerides, diglycerides, and triglycerides.

[191.] The present invention also provides for the method of any one of embodiments [179]-[181], wherein the biodiesel is separated from the reaction product and the one or more subsequent reaction products, and the biodiesel is distilled to provide purified biodiesel.

[192.] The present invention also provides for the method of any one of embodiments [179]-[191], wherein the biodiesel feedstock including triglycerides includes the esterification reaction product of any one of embodiments [52]-[118].

[193.] The present invention also provides for the method of any one of embodiments [179]-[191], wherein the biodiesel feedstock including triglycerides includes the final distillate of any one of embodiments [1]-[51].

[194.] The present invention also provides for the method of any one of embodiments [179]-[192], wherein the transesterification reaction product includes biodiesel, and includes one or more of the biodiesel impurities illustrated in Table A.

[195.] The present invention also provides for the method of any one of embodiments [179]-[192], wherein the transesterification reaction product includes biodiesel, and includes each of the biodiesel impurities illustrated in Table A.

[196.] The present invention also provides for the method of any one of embodiments [179]-[192], wherein the transesterification reaction product includes biodiesel, and includes one or more of the biodiesel impurities illustrated in Table A, each in the amount disclosed therein.

[197.] The present invention also provides for the method of any one of embodiments [179]-[192], wherein the transesterification reaction product includes biodiesel, and includes each of the biodiesel impurities illustrated in Table A, each in the amount disclosed therein.

[198.] The present invention also provides for the method of any one of embodiments [179]-[196], wherein the transesterification reaction product includes glycerin, and includes one or more of the biodiesel impurities illustrated in Table A.

[199.] The present invention also provides for the method of any one of embodiments [179]-[196], wherein the transesterification reaction product includes glycerin, and includes each of the biodiesel impurities illustrated in Table A.

[200.] The present invention also provides for the method of any one of embodiments [179]-[196], wherein the transesterification reaction product includes glycerin, and includes one or more of the biodiesel impurities illustrated in Table A, each in the amount disclosed therein.

[201.] The present invention also provides for the method of any one of embodiments [179]-[196], wherein the transesterification reaction product includes glycerin, and includes each of the biodiesel impurities illustrated in Table A, each in the amount disclosed therein.

TABLE A

| Impurities | | | | |
|---|---|---|---|---|
| | FEEDSTOCK [A] | PURIFIED BIODIESEL (PRODUCT) [B] | GLYCERIN (PRODUCT) [C] | |
| | | | In [D] | Out [E] |
| Aldehydes, Ketones | 30-5000 ppm | 2-8 ppm | | |
| Anisidine value | 20-90 AV | 2-5 AV | | |
| Ash | | | >0.2 wt. % | 0.002-0.006 wt. % |
| Calcium | 10-4,000 ppm | 1-4 ppm | | |
| Carboxylic acids | 100-2000 ppm | 1-8 ppm | | |
| Carotenes (red color) | 40-2,500 ppm | 2-20 ppm | | |
| Chloride | | | >2,000 ppm | 5-15 ppm |
| Chlorinated compounds | | | >5,000 ppm | 8-25 ppm |
| Chlorophylls (green color) | 300-1,600 ppm | 4-22 ppm | | |
| Cholesterol | 10-6,000 ppm | 4-15 ppm | | |
| Cobalt | 20-350 ppm | 2-6 ppm | | |
| Cold soak | N/A | 20-100 Seconds | | |
| Color | | | >12 APHA | <10 APHA |
| Copper | 10-500 ppm | 2-6 ppm | | |
| Degraded proteins and carbohydrates (brownish black color) | 0.1-0.2 wt. % | 0.001-0.005 wt. % | | |
| Dicarboxylic acid | 25-25,000 | 2-7 ppm | | |
| Diethylene glycol | | | >0.2 wt. % | 0.002-0.006 wt. % |
| Ethylene glycol | | | 0.50 wt. % | 0.002-0.006 wt. % |
| Fatty acid and esters | | | >0.5 wt. % | ≤1 ml of 0.5N NaOH consumed |
| Free glycerin | | 20-100 ppm | >70 wt. % by GC | ≥95 and ≤101 wt. % by GC |
| Heavy metals | | | >50 ppm | ≤4 ppm |
| Iron | 20-2000 ppm | 2-6 ppm | | |
| Lipids | 0.2-0.8 wt. % | 0.001%-0.0015 wt. % | | |
| Magnesium | 8-3000 ppm | 1-6 ppm | | |
| Manganese | 6-300 ppm | 1-4 ppm | | |
| Moisture | 0.2-99 wt. % | 10-50 ppm | | |
| Nickel | 5-400 ppm | 1-3 ppm | | |
| Perchloroethylene | 10-5000 ppm | 2-5 ppm | | |
| Peroxide value | 10-300 PV | 1-4 PV | | |
| Pesticides | 0.1-2 wt. % | 0.001-0.002 wt. % | | |
| Phospholipids (gums/unsaponfiables) (e.g., phosphatidylcholine, phosphatidylinositol, phosphatidic acid, and lysophosphatidic acid) | 20 ppm-30,000 ppm | 2-5 ppm | | |
| Phosphorus | 10-4000 ppm | 2-6 ppm | | |
| Phytosterols | 20-16,000 | 2-7 ppm | | |
| Polychlorinated cyclic hydrocarbons (e.g., polychloro benzene) | 20-6000 ppm | 2-8 ppm | | |
| Polycyclic aromatic hydrocarbons | 20-6000 ppm | 1-6 ppm | | |
| Polyethylene | 20-3000 ppm | 1-7 ppm | | |

TABLE A-continued

| | Impurities | | | |
|---|---|---|---|---|
| | FEEDSTOCK [A] | PURIFIED BIODIESEL (PRODUCT) [B] | GLYCERIN (PRODUCT) [C] | |
| | | | In [D] | Out [E] |
| Polymerized triglycerides | 0.1-6 wt. % | 0.001-0.002 wt. % | | |
| Potassium | 20-4000 ppm | 2-6 ppm | | |
| Sitosterols | 20-3000 ppm | 2-8 ppm | | |
| Soaps/Detergents | 30-4000 ppm | 1-6 ppm | | |
| Sodium | 10-3,500 ppm | 1-5 ppm | | |
| Solid particles | 0.02%-30 wt. % | 1-3 ppm | | |
| Specific gravity @ 25° C. | | | >0.90 | ≥1.249 |
| Sterol glucosides | 50-2500 ppm | 2-7 ppm | | |
| Sulfur, sulfates, suflides, sulfonates, and sulfones | 5 ppm-13,500 ppm | 1-5 ppm | >50 ppm | 10-15 ppm |
| Tocopherols | 8-2,650 ppm | 1-5 ppm | | |
| Tocotrienols | 3-800 ppm | 4-9 ppm | | |
| Total glycerin | n/a | 0.10-0.18 wt. % | | |
| Triglycerides | | 0.001-0.01 wt. % | | |
| Xantophylls (yellowish color) | 40-1200 ppm | 5-40 ppm | | |
| Water | | | >0.5 wt. % | 0.05 wt. %-0.20 wt. % |

[A] The values and ranges illustrated herein for the Feedstock are exemplary, as the nature and amount of impurities present will typically vary.
[B] The values and ranges illustrated herein for the Biodiesel are exemplary, as the nature and amount of impurities present will typically vary.
[C] The values and ranges illustrated herein for the Glycerin are exemplary, as the nature and amount of impurities present will typically vary.
[D] This refers to the crude glycerin obtained, prior to purification.
[E] This refers to the pure glycerin obtained, subsequent to purification.

The invention claimed is:

1. A method for transesterifying, with methanol, triglycerides present in a biodiesel feedstock comprising the steps in the order recited:
   (a) passing a filtered and dried biodiesel feedstock through a guard bed ion-exchange column, to remove undesired components;
   (b) contacting at a temperature of less than 102° F. (38.89° C.) (i) methanol, (ii) a solid heterogeneous transesterification enzyme catalyst immobilized on a solid support, and (iii) a biodiesel feedstock comprising triglycerides, wherein the contacting is carried out under conditions suitable to provide a transesterification reaction product comprising biodiesel, methanol, water, glycerin and optionally triglycerides;
   (c) separating water, glycerin and methanol from the transesterification reaction product;
   (d) contacting the transesterification reaction product with (i) methanol and (ii) a solid heterogeneous transesterification enzyme catalyst immobilized on a solid support, wherein the contacting is carried out under conditions suitable to provide a subsequent transesterification reaction product comprising biodiesel, methanol, water, glycerin and optionally triglycerides; and
   (e) separating water and methanol from the subsequent transesterification reaction product;
   wherein the methanol that is separated from the one or more transesterification reaction products is purified to a purity of at least about 99.9 wt. %, and is employed in a subsequent transesterification.

2. The method of claim 1, wherein the methanol is employed in at least a 5 molar or stoichiometric excess, relative to the triglycerides content of the biodiesel feedstock.

3. The method of claim 1, wherein the contacting is carried out at a temperature of 95° F. (35° C.), ±6° F.

4. The method of claim 1, wherein steps (a)-(e) are carried out in the absence of sodium methylate.

5. The method of claim 1, which comprises a first stage reactor and a second stage reactor.

6. The method of claim 1, wherein the methanol is employed in a stoichiometric excess, relative to the triglycerides content of the biodiesel feedstock.

7. The method of claim 1, wherein the methanol, catalyst, and biodiesel feedstock are heated for a period of time of up to about 75 minutes.

8. The method of claim 1, which provides for a crude reaction product comprising biodiesel, triglycerides, glycerin, methanol, and water;
   the method further comprising separating at least one of methanol and water from the crude reaction product, purifying the methanol, and reusing the purified methanol in a subsequent transesterification.

9. The method of claim 1, which provides for a crude reaction product comprising biodiesel, triglycerides, glycerin, methanol, and water;
   the method further comprising separating triglycerides from the crude reaction product and transferring the triglycerides to a second stage reactor and contacting the triglycerides with methanol having a purity of at least about 98 wt. % pure.

10. The method of claim 1, which provides for a crude reaction product comprising biodiesel, triglycerides, glycerin, methanol, and water;
    the method further comprising separating biodiesel and triglycerides from the crude reaction product and transferring the biodiesel and triglycerides to a second stage reactor and contacting the biodiesel and triglycerides with methanol having a purity of at least about 98 wt. % pure.

11. The method of claim 1, wherein the methanol is obtained from a previous transesterification.

12. The method of claim 1, wherein at least about 90 wt. % of the triglycerides present in the biodiesel feedstock are converted to the biodiesel.

13. The method of claim 1, carried out in a continuous fashion.

14. The method of claim 1, wherein triglycerides, diglycerides, and monoglycerides present in the biodiesel feedstock are transesterified with methanol, to provide a reaction product comprising biodiesel, glycerin, water, and un-reacted methanol.

15. The method of claim 1, wherein triglycerides, diglycerides, and monoglycerides present in the biodiesel feedstock are transesterified with methanol, to provide a reaction product comprising biodiesel, glycerin, water, un-reacted methanol, and optionally un-reacted triglycerides.

16. The method of claim 1, wherein triglycerides, diglycerides, and monoglycerides present in the biodiesel feedstock are transesterified with methanol, to provide a reaction product comprising biodiesel, glycerin, water, un-reacted methanol, and optionally un-reacted triglycerides; and
   at least one of methanol, water, and glycerin are separated from the reaction product.

17. The method of claim 1, wherein triglycerides present in the biodiesel feedstock are transesterified with methanol, to provide a reaction product comprising biodiesel, glycerin, water, un-reacted methanol, and optionally un-reacted triglycerides, diglycerides, and monoglycerides;
   at least one of methanol, water, and glycerin are separated from the reaction product; and
   the reaction product comprising biodiesel and un-reacted triglycerides, diglycerides, and monoglycerides are subsequently transesterified to provide a subsequent reaction product comprising biodiesel, glycerin, water, and un-reacted methanol.

18. The method of claim 1, wherein triglycerides present in the biodiesel feedstock are transesterified with methanol, to provide a reaction product comprising biodiesel, glycerin, water, un-reacted methanol, and optionally un-reacted triglycerides, diglycerides, and monoglycerides;
   at least one of methanol, water, and glycerin are separated from the reaction product;
   the reaction product comprising biodiesel and un-reacted triglycerides, diglycerides, and monoglycerides are subsequently transesterified to provide a subsequent reaction product comprising biodiesel, glycerin, water, and un-reacted methanol; and
   the separation and transesterification are optionally repeated one or more times.

19. The method of claim 1, wherein triglycerides present in the biodiesel feedstock are transesterified with methanol, to provide a reaction product comprising biodiesel, glycerin, water, un-reacted methanol, and optionally un-reacted triglycerides, diglycerides, and monoglycerides;
   at least one of methanol, water, and glycerin are separated from the reaction product;
   the reaction product comprising biodiesel and un-reacted triglycerides, diglycerides, and monoglycerides are subsequently transesterified to provide a subsequent reaction product comprising biodiesel, glycerin, water, and un-reacted methanol; and
the separation and transesterification are optionally repeated one or more times, until a further subsequent reaction product comprises no more than about 1 wt. % combined un-reacted triglycerides, diglycerides, and monoglycerides.

20. The method of claim 1, wherein the biodiesel is separated from the glycerin, and the purified biodiesel comprises less than about 2,000 ppmw of methanol.

21. The method of claim 1, wherein the biodiesel is separated from the glycerin, and the purified biodiesel comprises no more than about 0.12 wt. % of total glycerol.

22. The method of claim 1, wherein the biodiesel is separated from the glycerin, and the purified biodiesel comprises no more than about 200 ppmw of free glycerin.

23. The method of claim 1, wherein the biodiesel is separated from the glycerin, and the purified biodiesel comprises no more than about 0.2 acid number.

24. The method of claim 1, wherein the biodiesel is separated from the glycerin, and the purified biodiesel has a flash point of at least about 170° C.

25. The method of claim 1, wherein the biodiesel is separated from the glycerin, and the purified biodiesel has a moisture content of no more than about 50 ppmw.

26. The method of claim 1, wherein the biodiesel is separated from the glycerin, and the purified biodiesel has a sulfur content that is less than about 5 ppm.

27. The method of claim 1, wherein the biodiesel is separated from the glycerin, and the purified biodiesel has phosphorus content that is less than about 5 ppm.

28. The method of claim 1, wherein the biodiesel is separated from the glycerin, and the purified biodiesel has a content of polymerized triglycerides that is less than about 5 ppm.

29. The method of claim 1, wherein the biodiesel is separated from the glycerin, and the purified biodiesel has a sterols content that is less than about 10 ppm.

30. The method of claim 1, wherein steps (a)-(e) are carried out in the absence of a mineral acid.

\* \* \* \* \*